United States Patent
Pudil et al.

(10) Patent No.: US 9,974,896 B2
(45) Date of Patent: May 22, 2018

(54) METHOD OF ZIRCONIUM PHOSPHATE RECHARGING

(71) Applicant: Medtronic, Inc., Minneapolis, MN (US)

(72) Inventors: Bryant J. Pudil, Plymouth, MN (US); SuPing Lyu, Maple Grove, MN (US); Eric Grovender, Minneapolis, MN (US); Christopher M. Hobot, Tonka Bay, MN (US); Martin T. Gerber, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 412 days.

(21) Appl. No.: 14/642,847

(22) Filed: Mar. 10, 2015

(65) Prior Publication Data

US 2015/0367055 A1   Dec. 24, 2015

Related U.S. Application Data

(60) Provisional application No. 62/016,613, filed on Jun. 24, 2014, provisional application No. 62/077,159, filed on Nov. 7, 2014.

(51) Int. Cl.
*B01D 11/00* (2006.01)
*A61M 1/16* (2006.01)
(Continued)

(52) U.S. Cl.
CPC ............ *A61M 1/1696* (2013.01); *B01J 39/09* (2017.01); *C01B 25/45* (2013.01)

(58) Field of Classification Search
None
See application file for complete search history.

(56) References Cited

U.S. PATENT DOCUMENTS 3,850,835 A   11/1974  Marantz
4,192,748 A    3/1980  Hyden
(Continued)

FOREIGN PATENT DOCUMENTS

EP      2446908      5/2012
JP      S5070281 A   6/1975
(Continued)

OTHER PUBLICATIONS

Office Action in App. No. AU 2015280604 dated Apr. 8, 2016.
(Continued)

*Primary Examiner* — Richard C Gurtowski
(74) *Attorney, Agent, or Firm* — Kenneth Collier; Roger Hahn

(57) ABSTRACT

Methods and related apparatuses for sorbent recharging are provided. The methods and related apparatuses for recharging can recharge a specific rechargeable layer of a sorbent material such as zirconium phosphate in a sorbent cartridge. The methods and apparatuses include passing solutions containing combinations of acids, bases and salts through a module containing a rechargeable sorbent material such as zirconium phosphate in order to replace ions bound to the zirconium phosphate with hydrogen and sodium ions. The method allows for a customizable zirconium phosphate, with control over the ratios of sodium to hydrogen on the recharged zirconium phosphate.

20 Claims, 11 Drawing Sheets

(51) Int. Cl.
*C01B 25/45* (2006.01)
*B01J 39/09* (2017.01)

(56) References Cited

U.S. PATENT DOCUMENTS

| | | |
|---|---|---|
| 6,579,460 B1 | 6/2003 | Willis |
| 2002/0112609 A1 | 8/2002 | Wong |
| 2003/0097086 A1 | 5/2003 | Gura |
| 2005/0056592 A1 | 3/2005 | Braunger |
| 2005/0274658 A1 | 12/2005 | Rosenbaum |
| 2006/0241543 A1 | 10/2006 | Gura |
| 2008/0011664 A1 | 1/2008 | Karoor |
| 2008/0241031 A1 | 10/2008 | Li |
| 2009/0101552 A1 | 4/2009 | Fulkerson |
| 2009/0282980 A1 | 11/2009 | Gura |
| 2010/0004588 A1 | 1/2010 | Yeh |
| 2010/0078387 A1 | 4/2010 | Wong |
| 2010/0312172 A1 | 12/2010 | Hoffman |
| 2011/0017665 A1 | 1/2011 | Updyke |
| 2011/0048949 A1 | 3/2011 | Ding |
| 2011/0171713 A1 | 7/2011 | Bluchel |
| 2011/0272352 A1 | 11/2011 | Braig |
| 2011/0297593 A1 | 12/2011 | Kelly |
| 2012/0273354 A1 | 11/2012 | Orhan et al. |
| 2013/0199998 A1 | 8/2013 | Kelly |
| 2013/0213890 A1 | 8/2013 | Kelly |
| 2014/0158588 A1 | 6/2014 | Pudil |
| 2014/0158623 A1 | 6/2014 | Pudil |
| 2015/0108069 A1* | 4/2015 | Merchant ............ A61M 1/1696 210/681 |
| 2015/0251161 A1 | 9/2015 | Pudil |
| 2015/0251162 A1 | 9/2015 | Pudil |
| 2015/0367055 A1 | 12/2015 | Pudil |

FOREIGN PATENT DOCUMENTS

| | | |
|---|---|---|
| JP | 2981573 | 11/1999 |
| WO | 200744602 | 2/2007 |
| WO | 2013-025957 | 2/2013 |
| WO | 2013-028809 | 2/2013 |
| WO | WO 2013/019994 | 2/2013 |
| WO | WO 2013019179 | 2/2013 |
| WO | 2013101888 | 7/2013 |
| WO | WO 2013/103607 | 7/2013 |
| WO | 2015060914 | 4/2015 |
| WO | 2015199765 | 12/2015 |
| WO | 2015199863 | 12/2015 |
| WO | 2015199864 | 12/2015 |

OTHER PUBLICATIONS

Wester et al., A regenerable postassium and phosphate sorbent system to enhance dialysis efficacy and device portability: an in vitro study Nephrol Dial Transplant (2013) 28: 2364-2371 Jul. 3, 2013.
John Wm Agar: "Review: Understanding sorbent dialysis systems," Nephrology, vol. 15, No. 4, Jun. 1, 2010, pp. 406-411.
Office Action in App. No. JP 2016-515476 dated Dec. 26, 2016.
PCT/US2015/032494 Written Opinion dated Nov. 19, 2015.
PCT/US2015/032494 International Search Report dated Nov. 19, 2015.
PCT/US2015/019901 International Preliminary Report on Patentability dated May 27, 2016.
PCT/US2015/032485 International Preliminary Report on Patentability dated May 11, 2016.
PCT/US2016/030304 International Search Report dated Jul. 27, 2016.
PCT/US2016/030304 Written Opinion dated Jul. 27, 2016.
PCT/US2016/030312 Written Opinion dated Jul. 28, 2016.
PCT/US2016/030312 International Search Report dated Jul. 28, 2016.
PCT/US2016/030319 Written Opinion dated Jul. 27, 2016.
PCT/US2016/030319 International Search Report dated Jul. 27, 2016.
PCT/US2016/030320 International Search Report dated Jul. 28, 2016.
PCT/US2016/030320 Written Opinion dated Jul. 28, 2016.
PCT/US2015/032485 Written Opinion dated Oct. 16, 2016.
PCT/US2015/032485 International Search Report and Written Opinion dated Oct. 16, 2015.
PCT/US2016/030320 International Preliminary Report on Patentability, dated Apr. 20, 2017.
PCT/US2015/019901 International Search Report and Written Opinion dated Jun. 5, 2015.
PCT/US2015/032494 International Preliminary Report on Patentablity dated Dec. 27, 2016.
PCT/US2015/032492 International Search Report dated Nov. 19, 2015.
PCT/US2015/032492 Written Opinion dated Nov. 19, 2015.
Wheaton, et al., Dowex Ion Exchange Resins-Fundamentals of Ion Exchange; Jun. 2000, pp. 1-9. http://www.dow.com/scripts/litorder.asp?filepath=liquidseps/pdfs/noreg/177-01837.pdf.
European Search Report and Supplemental Search Report in European Application No. 14865374.4 dated Jun. 12, 2017.
Search Report in EP App. No. 15752771, dated Nov. 22, 2017.
[NPL603] Japanese Patent Publication No. S50-70281A.
PCT/US2016/030304_IPRP.
PCT/US2016/030319_IPRP.
European Search Report for EP App. No. 15811326.6, dated Feb. 12, 2018.
European Search Report for EP App. No. 15812413.1, dated Feb. 2, 2018.

* cited by examiner

METHOD OF ZIRCONIUM PHOSPHATE RECHARGING

FIELD OF THE INVENTION

The invention relates to a method and related apparatus for sorbent recharging, and recharging zirconium phosphate, in particular. The method and related apparatus for recharging can recharge a specific rechargeable layer of a sorbent material in a sorbent cartridge such as zirconium phosphate. The zirconium phosphate may be recharged by passing a solution or solutions through the zirconium phosphate wherein the solution(s) contain appropriate solutes. The zirconium phosphate may be included in a sorbent cartridge, and the zirconium phosphate may be recharged without removing the zirconium phosphate from the sorbent cartridge.

BACKGROUND

Zirconium phosphate is a common material used in sorbent cartridges for sorbent dialysis. Zirconium phosphate can remove ammonium ions from spent dialysate, generated by the breakdown of urea in the spent dialysate by urease, as well as potassium, calcium, and magnesium ions from spent dialysate. Known sorbent dialysis systems do not provide for a way to recharge the zirconium phosphate present in a sorbent cartridge so that the zirconium phosphate can be reused for future dialysis sessions. Instead, known sorbent dialysis systems generally require the sorbent materials to be discarded and the sorbent cartridge replaced after each use. The discarding and replacement of expensive sorbent materials, such as zirconium phosphate, increases both costs and waste.

Zirconium phosphate operates by exchanging sodium and/or hydrogen ions bound to the zirconium phosphate for ammonium, potassium, calcium, magnesium and other cations present in spent dialysate. The ratio of sodium to hydrogen ions released by the zirconium phosphate into the dialysate may depend on the ratio originally bound to the zirconium phosphate. Known systems do not provide for a method whereby the ratio of sodium to hydrogen ions bound to the zirconium phosphate can be varied depending on the particular needs of each patient. Known sorbent dialysis systems do not involve the use of separate modules for the purpose of separating rechargeable sorbent materials, such as zirconium phosphate, from non-rechargeable materials, such as urease.

As such, there is a need for systems and methods for recharging sorbent materials such as zirconium phosphate for reuse. There is also a need for methods and systems for separating sorbent materials within a sorbent cartridge into single and multi-use modules that can facilitate recharging and reuse of at least one of the sorbent materials. There is further a need for systems and related methods whereby rechargeable sorbent materials can be separated into multi-use modules and single-use modules wherein non-rechargeable sorbent materials can optionally be contained in the single-use modules. There is also a need for a method of controlling the ratio of sodium to hydrogen ions bound to the zirconium phosphate, and changing the ratio based on physiological parameters obtained from a patient.

SUMMARY OF THE INVENTION

The first aspect of the invention relates to a method of recharging zirconium phosphate. In any embodiment of the first aspect of the invention, the method can comprise the steps of recharging zirconium phosphate by passing a solution of any one of an acid, a sodium salt, and combinations thereof, through the zirconium phosphate.

In any embodiment of the first aspect of the invention, the zirconium phosphate can be contained in a rechargeable sorbent cartridge module.

In any embodiment of the first aspect of the invention, the rechargeable sorbent cartridge module can be capable of being detachably connected to at least one other sorbent cartridge module such that the modules are in fluid communication when connected.

In any embodiment of the first aspect of the invention, the sodium salt can be selected from the group consisting of sodium chloride, sodium acetate, sodium phosphate, sodium sulfate, sodium carbonate, sodium nitrate, and sodium citrate.

In any embodiment of the first aspect of the invention, the concentration of the sodium salt passed through the zirconium phosphate can be between any of 0.05 M to saturated, 0.05 M to 1.5 M, 1 M to 2.0 M, 1.8 M to 3.5 M, or 3.0 M to 5.0 M.

In any embodiment of the first aspect of the invention, the volume of the solution passed through the zirconium phosphate can be between any of 0.5 mL per gram of zirconium phosphate to 30 mL per gram of zirconium phosphate, 1.0 mL per gram of zirconium phosphate to 10 mL per gram of zirconium phosphate, 3.0 mL per gram of zirconium phosphate to 15 mL per gram of zirconium phosphate, and 0.5 mL per gram of zirconium phosphate to 20 mL per gram of zirconium phosphate.

In any embodiment of the first aspect of the invention, the method can comprise maintaining the temperature of the solution of any one of an acid, a sodium salt, and combinations thereof, at between about 20° C. and about 105° C.

In any embodiment of the first aspect of the invention, the flow rate of the solution passed through the zirconium phosphate can be between any of 0.01 to 9.0 ml/min per gram of zirconium phosphate, 0.1 to 1 ml/min per gram of zirconium phosphate, 0.5 to 2.0 ml/min per gram of zirconium phosphate, 1.5 to 4.0 ml/min per gram of zirconium phosphate, and 3.0 to 7.0 ml/min per gram of zirconium phosphate.

In any embodiment of the first aspect of the invention, the method can comprise halting the flow of the solution passed through the zirconium phosphate at least once, retaining the solution in the zirconium phosphate for a pre-set period of time, and re-starting the flow of the solution passing through the zirconium phosphate after the pre-set period of time.

In any embodiment of the first aspect of the invention, the direction of flow of the solution through the zirconium phosphate can be in an opposite direction of a flow of spent dialysate directed through the zirconium phosphate during a dialysis session.

In any embodiment of the first aspect of the invention, the acid can be selected from the group consisting of sulfuric acid, phosphoric acid, citric acid, acetic acid, formic acid, lactic acid, and hydrochloric acid.

In any embodiment of the first aspect of the invention, the acid concentration can be between any of 1 mM and 5000 mM, 15 mM to 500 mM, 100 mM to 2500 mM, 250 mM to 4000 mM, or 500 mM to 5000 mM.

In any embodiment of the first aspect of the invention, the solution of a sodium salt can be passed through the zirconium phosphate prior to the solution of acid passed through the zirconium phosphate.

In any embodiment of the first aspect of the invention, the method can comprise passing a solution of sodium hydroxide and sodium carbonate through the zirconium phosphate after the step of passing the acid solution through the zirconium phosphate.

In any embodiment of the first aspect of the invention, the solution of acid can have a concentration between any of 0.05 M to saturated, 0.05 M to 0.2 M, 0.1 M to 0.3 M, 0.2 M to 1 M, or 0.8 M to 5.0 M; and the solution of sodium hydroxide and sodium carbonate can have a concentration between any of 0.05 M to saturated, 0.05 M to 0.2 M, 0.1 M to 0.3 M, 0.2 M to 1 M, or 0.8 M to 5.0 M.

In any embodiment of the first aspect of the invention, the ratio of sodium hydroxide to sodium carbonate can be between any of 0 to 3, 0.5 to 1.5, 1 to 2 or 1.5 to 3.0.

In any embodiment of the first aspect of the invention, the method can comprise adding a water miscible organic solvent to the solution passed through the zirconium phosphate.

In any embodiment of the first aspect of the invention, the method can comprise filtering the solution after passing through the zirconium phosphate and reusing the solution.

In any embodiment of the first aspect of the invention, the water miscible organic solvent can be selected from the group consisting of methanol, ethanol, isopropanol, and acetone.

In any embodiment of the first aspect of the invention, the method can comprise using at least a portion of the solution passed through the zirconium phosphate to recharge zirconium phosphate, and passing the portion of the solution through the zirconium phosphate at least one more time.

In any embodiment of the first aspect of the invention, at least a portion of the solution passed through the zirconium phosphate can comprise ultrafiltrate collected during a dialysis session, wherein the ultrafiltrate comprises fluid that has passed through a sorbent cartridge, and wherein the ultrafiltrate does not comprise potassium, magnesium, calcium or ammonium.

In any embodiment of the first aspect of the invention, the ultrafiltrate can be collected from dialysate after the dialysate passed through a sorbent cartridge and additional sodium salts can be added to create the solution passed through the zirconium phosphate.

The second aspect of the invention is drawn to method of recharging zirconium phosphate. In any embodiment of the second aspect of the invention, the method can comprise recharging zirconium phosphate by passing a buffer solution comprising an acid and a sodium salt of a conjugate base of the acid through the zirconium phosphate.

In any embodiment of the second aspect of the invention, the buffer solution can be selected from the group consisting of sodium acetate and acetic acid, sodium monobasic-phosphate and sodium dibasic-phosphate, and sodium citrate and citric acid.

In any embodiment of the second aspect of the invention, the ratio of the concentrations of the acid to the conjugate base can be determined by a ratio of hydrogen to sodium ions desired on the zirconium phosphate after recharging.

In any embodiment of the second aspect of the invention, the method can comprise adding sodium chloride to the buffer solution.

In any embodiment of the second aspect of the invention, about 3 mL of buffer solution per gram of zirconium phosphate can be passed through the zirconium phosphate. The buffer solution can comprise about 3340 mM of NaCl, about 220 mM of sodium citrate tribasic, and about 60 mM of citric acid. The temperature of the buffer solution can be at about 80° C. The flow rate of the buffer solution passing through the zirconium phosphate can be about 0.1 mL/min per gram of zirconium phosphate. The direction of flow of the buffer solution through the zirconium phosphate can be in an opposite direction as a direction of flow of dialysate through the zirconium phosphate during a dialysis session.

In any embodiment of the second aspect of the invention, the zirconium phosphate can be loaded with about 1 mEq of cations per gram of zirconium phosphate.

In any embodiment of the second aspect of the invention, the pH of the buffer solution is between any of about 4 and about 8, about 4.5 and about 6, about 6 and about 7, or about 5.5 and about 7.5.

In any embodiment of the second aspect of the invention, the method can further comprise passing a solution of a sodium salt through the zirconium phosphate prior to the step of passing the buffer solution through the zirconium phosphate.

The third aspect of the invention relates to a method of recharging zirconium phosphate that can comprise recharging zirconium phosphate by passing a solution of sodium hydroxide and sodium bicarbonate through the zirconium phosphate.

In any embodiment of the third aspect of the invention, the concentration of the solution of sodium hydroxide and sodium bicarbonate can be between any of 0.05 M to saturated, 0.05 M to 0.2 M, 0.1 M to 0.3 M, 0.2 M to 1 M, or 0.8 M to 5.0 M.

In any embodiment of the third aspect of the invention, the ratio of sodium hydroxide to sodium bicarbonate can be between any of 0 to 3, 0 to 1, 0.5 to 1.5, 1 to 2 or 1.5 to 3.

In any embodiment of the third aspect of the invention, the solution of sodium hydroxide and sodium bicarbonate can be recirculated, and the method can further comprise degassing the solution of sodium hydroxide and sodium bicarbonate, filtering the solution of sodium hydroxide and sodium bicarbonate, or both.

In any embodiment of the third aspect of the invention, the method can comprise storing the zirconium phosphate after the recharging the zirconium phosphate, wherein the zirconium phosphate can be stored by filling a module containing the zirconium phosphate with a buffer solution, wherein the buffer solution has a pH between about 6 to about 8.

In any embodiment of the first, second or third aspects of the invention, the sorbent cartridges and dialysis systems and related methods of the present invention can be used as part or operated in conjunction with a controlled compliant dialysis flow path.

DETAILED DESCRIPTION OF THE INVENTION

Figure 1:
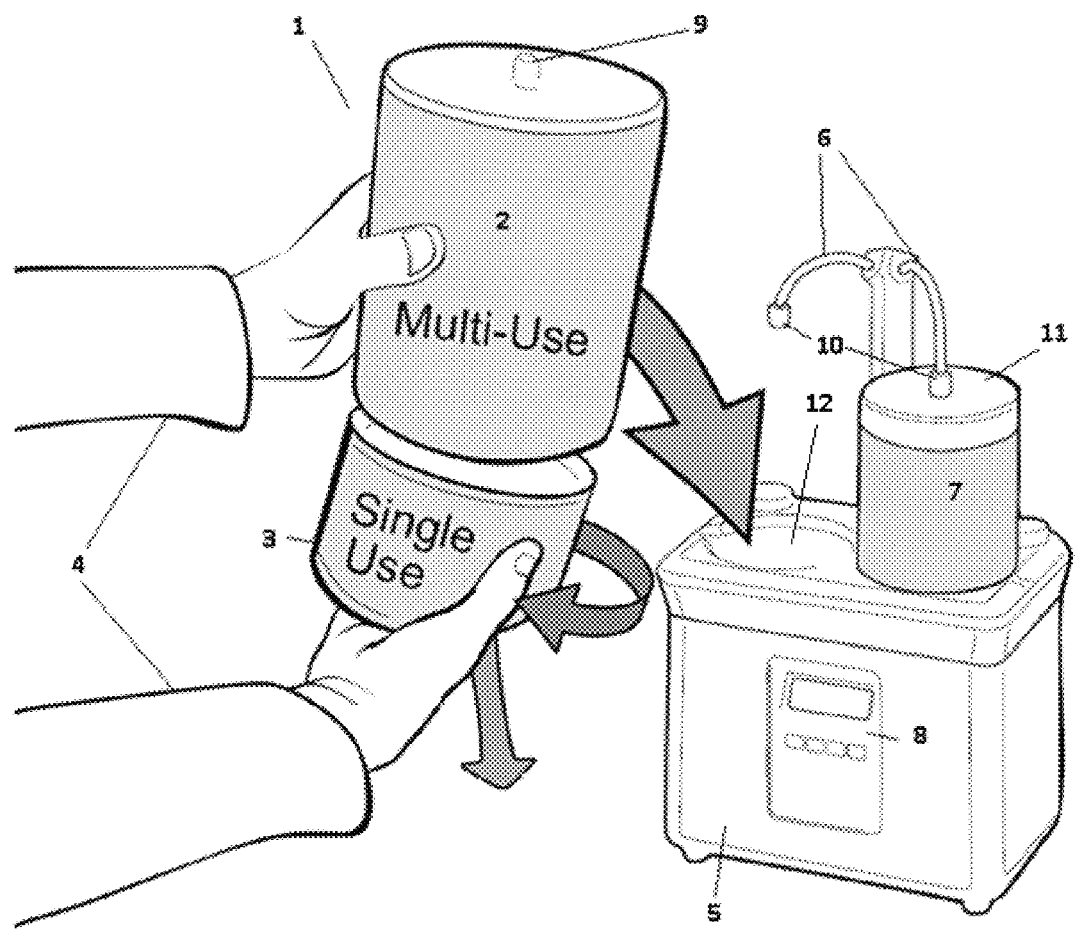
FIG. 1 shows a representative set up for the method of the invention.

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. By way of example, "an element" means one element or more than one element.

An "acid" as used herein can be either a Lewis acid or a Brønsted-Lowry acid. A Lewis acid is a compound that is capable of accepting a lone pair of electrons. A Brønsted-Lowry acid is a compound that is capable of donating a hydrogen ion to another compound.

A "buffer solution" is a solution comprising a weak acid and the conjugate base of the weak acid.

The term "cartridge" refers to any container designed to contain a powder, fluid, or gas made for ready connection to a device, structure, system, flow path, or mechanism. The container can have one or more compartments. Instead of compartments, the container can also be comprised of a system of two or more modules connected together to form the cartridge wherein the two or more modules once formed can be connected to a device, structure, system, flow path, or mechanism.

The term "comprising" includes, but is not limited to, whatever follows the word "comprising." Thus, use of the term indicates that the listed elements are required or mandatory but that other elements are optional and may or may not be present.

"Conjugate base" refers to the compound formed after an acid donates a hydrogen ion to another compound.

The term "consisting of" includes and is limited to whatever follows the phrase "consisting of." Thus, the phrase indicates that the limited elements are required or mandatory and that no other elements may be present. The term "consisting essentially of" includes whatever follows the term "consisting essentially of" and additional elements, structures, acts or features that do not affect the basic operation of the apparatus, structure or method described.

The term "contain" as used herein means to keep a material within a specific place. "Contain" can refer to materials that are placed within a component, absorbed onto a component, bound to a component, or any other method of keeping the material in a specific place.

The term "container" as used herein is a receptacle that may be flexible or inflexible for holding any fluid or solid, such as for example a spent dialysate fluid, or a sodium chloride or sodium bicarbonate solution or solid, or urease, or urease/alumina, and the like. A "sorbent container" is any receptacle configured to hold one or more sorbent materials. Similarly, a "urease container" is any receptacle configured to hold urease.

The terms "detachable," "detached," or "detachably" relate to any component of the present invention that can be separated from a system, module, cartridge or any component of the invention. "Detachable" can also refer to a component that can be taken out of a larger system with minimal time or effort. In certain instances, the components can be detached with minimal time or effort, but in other instances can require additional effort. The detached component can be optionally reattached to the system, module, cartridge or other component. A detachable module can often be part of a reusable module.

"Dialysate" is the fluid that passes through the dialyzer on the side of the dialysis membrane that is opposite to the fluid (e.g. blood) that is being dialyzed.

"Dialysate regeneration" refers to the process of treating spent dialysate, containing solutes removed from the patient's blood, with one or more sorbent materials in order to remove specific solutes, such as urea, and thereby generate dialysate that can be reused for dialysis.

"Dialysis" is a type of filtration, or a process of selective diffusion through a membrane. Dialysis removes solutes of a specific range of molecular weights via diffusion through a membrane from a fluid to be dialyzed into a dialysate. During dialysis, a fluid to be dialyzed is passed over a filter membrane, while dialysate is passed over the other side of that membrane. Dissolved solutes are transported across the filter membrane by diffusion between the fluids. The dialysate is used to remove solutes from the fluid to be dialyzed. The dialysate can also provide enrichment to the other fluid.

A "dialysis flow path" is the route in which a fluid will travel during dialysis.

A "dialysis session" refers to the medical procedure wherein dialysis is preformed on a patient.

The term "dialyzer" refers to a cartridge or container with two flow paths separated by semi-permeable membranes. One flow path is for blood and one flow path is for dialysate. The membranes can be in the form of hollow fibers, flat sheets, or spiral wound or other conventional forms known to those of skill in the art. Membranes can be selected from the following materials of polysulfone, polyethersulfone, poly(methyl methacrylate), modified cellulose, or other materials known to those skilled in the art.

"Flow" refers to the movement of a fluid or a gas.

A "fluid" is a liquid substance optionally having a combination of gas and liquid phases in the fluid. Notably, a liquid, as used herein, can therefore also have a mixture of gas and liquid phases of matter.

The term "fluid communication" refers to the ability of fluid or gas to move from one component or compartment to another within a system or the state of being connected, such that fluid or gas can move by pressure differences from one portion that is connected to another portion.

The term "fluidly connectable" refers to the ability of providing for the passage of fluid or gas from one point to another point. The two points can be within or between any one or more of compartments, modules, systems, components, and rechargers, all of any type.

"Functional capacity" is the ability of a material to accomplish the material's intended function. In some instances functional capacity can refer to the ability of a sorbent material to remove specific ions from a fluid, or to transform specific solutes into other materials.

"Module" refers to a discreet component of a system. Each of the modules can be fitted to each other to form a system of two or more modules. Once fitted together, the modules can be in fluid connection and resist inadvertent disconnection. A single module can represent a cartridge to be fitted to a device or mechanism if the module is designed to contain all the necessary components for an intended purpose such as a sorbent for use in dialysis. In such a case, the module can be comprised of one or more compartments within the module. Alternatively, two or more modules can form a cartridge to be fitted to a device or mechanism where each module individually carries separate components but only when connected together contain in summation all the necessary components for an intended purpose such as a sorbent for use in dialysis. A module can be referred to as a "first module," "second module," "third module," etc. to refer to any number of modules. The designation of "first," "second," "third," etc. does not refer to the respective placement of the module in the direction of fluid or gas flow, and merely serves to distinguish one module from another unless otherwise indicated.

A "multi-use module" is a module that can be used for more than one dialysis session, often with recharging of the sorbent materials inside the module between uses.

The terms "pathway," "conveyance pathway," "fluid flow path," and "flow path" refer to the route through which a fluid or a gas, such as dialysate or blood, travels, or the route a gas travels.

"Recharging" refers to the process of treating a sorbent material to restore the functional capacity of the sorbent material so as to put the sorbent material back into a condition for reuse or use in a new dialysis session. In some instances, the total mass, weight and/or amount of "rechargeable" sorbent materials remain the same. In some instances, the total mass, weight and/or amount of "rechargeable" sorbent materials change. Without being limited to any one theory of invention, the recharging process may involve exchanging ions bound to the sorbent material with different ions, which in some instances may increase or decrease the total mass of the system. However, the total amount of the sorbent material will in some instances be unchanged by the recharging process. Upon a sorbent material undergoing "recharging," the sorbent material can then be said to be "recharged." Recharging of rechargeable sorbent materials is not the same as replenishing of a particular sorbent material such as urease. Notably, urease is not generally "recharged," but can be replenished, as defined herein.

"Replenishing" means to add back into a system, section or module, a material that was previously removed, reduced, depleted, or taken out from that system, section or module. For example, after introducing an amount of a sorbent material, e.g., urease, that was reduced in quantity and/or functional capacity in a compartment, the compartment with the freshly introduced sorbent material can then be said to be "replenished."

"Reusable" or "reusing" refers in one instance to a solid, liquid, gas that can be used more than one time, optionally with treatment of any type of the material between uses. For example, a material and a solution can be reused. In one instance, reusable can refer to a cartridge, as used herein, that contains a material that can be recharged by recharging the material(s) contained within the cartridge.

"Saturated" refers to a solution containing the maximum possible amount of a particular solute at a given temperature.

A "section" refers to any portion of a larger component. A section can be referred to as a "first section," "second section," "third section," etc. to refer to any number of sections. The designation of "first," "second," "third," etc. does not refer to the respective placement of the section in the direction of fluid or gas flow, and merely serves to distinguish one section from another unless otherwise indicated. Additionally, each section can be optionally physically separated such as by a divider or wall; however, referring to a particular section does not necessarily require physical separation and merely refer to a particular location in which a material is contained.

A "single-use module" is a module that contains sorbent materials that are not intended to be recharged. A "single-use" module can be used more than one time, but requires replenishing or refilling of the sorbent materials inside.

A "sodium salt" is an ionic compound made up of at least one sodium ion and at least one anion, wherein the ratio of sodium ions to anions is based on the charge of the anion, in order to achieve an electrically neutral compound.

A "solution," as used herein is a homogeneous mixture comprising a solvent and at least one solute, wherein the solute is dissolved in the solvent.

"Sorbent cartridge" refers to a cartridge that can contain one or more sorbent materials. The cartridge can be connected to a dialysis flow path. The sorbent materials in the sorbent cartridge are used for removing specific solutes from solution, such as urea. The sorbent cartridge can have a single compartmental design wherein all sorbent materials necessary for performing dialysis are contained within the single compartment. Alternatively, the sorbent cartridge can have a modular design wherein the sorbent materials are dispersed across at least two different modules, which can be connected to form a unitary body. Once the at least two modules are connected together, the connected modules can be referred to as a sorbent cartridge, which can be fitted to a device or mechanism. When a single module contains all the sorbent materials necessary for performing dialysis, the single module can be referred to as a sorbent cartridge.

A "sorbent cartridge module" means a discreet component of a sorbent cartridge. Multiple sorbent cartridge modules can be fitted together to form a sorbent cartridge of two or more sorbent cartridge modules. In some embodiments, a single sorbent cartridge module can contain all of the necessary materials for use in dialysis. In such cases, the sorbent cartridge module can be considered to be a "sorbent cartridge."

"Sorbent materials" are materials capable of removing specific solutes from solution, such as urea.

A "sorbent module" is a container containing at least one sorbent material. In some embodiments, the sorbent module can connect to another sorbent module to form a sorbent cartridge.

"Spent dialysate" is a dialysate contacted with blood through a dialysis membrane and contains one or more impurity, or waste species, or waste substance, such as urea.

The terms "waste species," "waste products," "waste," or "impurity species" refer to any molecular or ionic species originating from the patient or subject, including metabolic wastes, molecular or ionic species including nitrogen or sulfur atoms, mid-weight uremic wastes and nitrogenous waste. Waste species are kept within a specific homeostasis range by individuals with a healthy renal system.

The term "water miscible" describes a property of a gas, solid, or liquid to mix in water to form a solution.

Zirconium Phosphate Recharging

The first, second and third aspects of the invention provide for methods and related apparatuses for recharging a rechargeable sorbent material. The rechargeable sorbent material can be one or more and includes the group of zirconium phosphate, activated carbon, zirconium oxide, and rechargeable sorbent materials as defined herein. In particular, the first, second and third aspects of the invention provide for a method and apparatus for recharging zirconium phosphate used in dialysis systems that can displace any ammonium, potassium, calcium, magnesium, or other cations from the zirconium phosphate and replace them with sodium and/or hydrogen ions. By recharging the rechargeable sorbent material, and in particular, zirconium phosphate, in this manner, the rechargeable sorbent material, such as zirconium phosphate can be reused instead of discarded, reducing costs and waste. The rechargeable sorbent material such as zirconium phosphate may be part of a sorbent dialysis system. In particular, zirconium phosphate can be used to remove ammonium ions in spent dialysate generated by the breakdown of urea to ammonia and carbon dioxide by urease also present in the sorbent dialysis system. By allowing the zirconium phosphate to be recharged after use, the first, second and third aspects of the invention allow a sorbent cartridge or module containing the zirconium phosphate to also be reused more than once.

FIG. 1 shows an embodiment of a process of recharging a sorbent module of the first, second and third aspects of the invention, having a rechargeable sorbent material, specifically, zirconium phosphate. As shown in FIG. 1, the sorbent cartridge 1 can be a modular dialysate regeneration assembly. In general, a modular dialysate regeneration assembly can be one or more sorbent compartments containing at least one sorbent material attached to at least another sorbent compartment. That is, the sorbent cartridge 1 can comprise multiple modules. Each module can be detachably connected to the other module or modules. The modules, when attached can form a fluid connection as described herein to allow fluid to flow from one module into another. The modules can be detached as shown in FIG. 1 into separate components to facilitate the recharging of rechargeable sorbent materials. The sorbent cartridge 1 may contain a multi-use module 2 which contains zirconium phosphate, and a single-use module 3 which comprises other sorbent materials, such as activated carbon, alumina, silica, urease, hydrous zirconium oxide and ion-exchange resin. Single use module 3 can also contain zirconium phosphate that is not intended to be recharged. In any embodiment of the first, second and third aspects of the invention, the sorbent cartridge 1 can be a single structure, with all sorbent materials in the same module. After use, the functional capacity of the modules may be reduced due to the binding of solutes from spent dialysate to the sorbent materials within the sorbent cartridge. The user 4 can disconnect the single-use module 3 from the multi-use module 2. The single use module can be discarded or sent to a recharging or replenishing facility for recharging or replenishing. The multi-use module 2 can be recharged in order to restore the functional capacity of the sorbent materials as described herein. The multi-use module 2 can also be replenished to add back sorbent materials into the multi-use module 2. Sorbent systems with multiple modules are described in detail in U.S. application Ser. No. 14/261,651, filed on Apr. 25, 2014, and the contents thereof incorporated herein by their entirety.

As shown in FIG. 1, the recharging apparatus 5 can comprise a sorbent cartridge fluid inlet 6 and a sorbent cartridge fluid outlet (not shown), as shown by recharging sorbent module 7. The fluid inlet 6 can connect to the modules by attaching recharger connector 10 to sorbent module connector 9 (only shown for module 2). The proper solutions as described herein can pass through the multi-use modules as needed, such as with multi-use module 7 located on the recharging apparatus 5. Interface 8 can be used to notify the user of the progress of the recharging process, or can be used by the user to select the proper solutions, concentrations, amounts, temperature or other variables described herein for the recharging process. In any embodiment of the first, second and third aspects of the invention, instead of the recharge connector 10 attaching directly to connector 9 on the multi use module 2, a separate connector 11 can be fitted to the multi use module, as is shown with multi use module 7. This connector 11 can fit over the top of the multi use module 7 and facilitate the introduction of recharging solution into the multi-use module 7.

In any embodiment of the first, second and third aspects of the invention, the recharging solution can be recirculated. Solution that enters through the top connector 10 of the multi-use module 7 can exit the multi-use module 7 through the bottom and enter the basin of the recharging apparatus 5. The solution, in any embodiment of the first, second and third aspects of the invention, can then be passed back to the fluid inlet 6 and back into the multi-use module 7. A pump (not shown) in the base of the recharging apparatus 5 can be used to pump the solution back to fluid inlet 6 for re-entry into multi-use module 7, forming a fluid flow loop. In any embodiment of the first, second and third aspects of the invention, the solution can be treated before the solution is passed back into the multi use module 7 as explained herein.

In any embodiment of the first, second and third aspects of the invention, the recharger 5 can accommodate multiple multi-use sorbent modules at the same time, such as both multi use sorbent modules 2 and 7 as shown in FIG. 1. Multi-use sorbent module 2 can be placed in space 12 while the recharging apparatus 5 is recharging multi use module 7. One skilled in the art will understand that the invention is not limited to recharging systems that can accommodate two multi-use modules at the same time. Systems that can only accommodate a single multi-use module, as well as systems that can accommodate 3, 4, 5, or more multi-use modules simultaneously are contemplated by this invention.

The multi-use modules can connect to the recharger by any means known in the art. In any embodiment of the first, second and third aspects of the invention, the connection can be a screw type connection, wherein the multi-use module 2 can be placed in space 12 of FIG. 1 and twisted to lock the multi-use module 2 into the recharging apparatus 5. In any embodiment of the first, second and third aspects of the invention, the space 12 on the recharging apparatus 5 may be nearly the same circumference as the multi-use module 2. When the multi-use module 2 is placed into the space 12, the multi-use module 2 contacts the edges of space 12 and a seal can be formed between the edges of the space 12 and the multi-use module 2. In any embodiment of the first, second and third aspects of the invention, an o-ring, gasket or other sealing means can be used to ensure that there is no fluid leakage. Other fluid connections are described herein.

In any embodiment of the first, second and third aspects of the invention, the recharging solution can be passed through the multi-use module in the opposite direction that spent dialysate travels through the module during dialysis. Passing the recharging solution through in the opposite direction may result in a more efficient recharging process, as explained herein. In any embodiment of the first, second and third aspects of the invention, the recharging solution can be passed through the module in the same direction as spent dialysate during a dialysis session.

Figure 2:
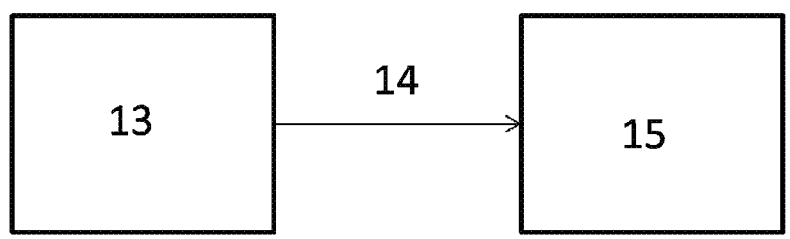
FIG. 2 shows a method of recharging zirconium phosphate by passing a single solution through the zirconium phosphate.

One non-limiting embodiment of a method for recharging zirconium phosphate of the first, second and third aspects of the invention is shown in FIG. 2. The process can begin with a multi-use module containing zirconium phosphate 13, which before recharging may contain potassium, calcium, magnesium, ammonium, or other cations bound to the zirconium phosphate. A recharging solution made of a concentrated solution of a sodium salt can be passed through the zirconium phosphate in step 14. The high sodium concentration in the recharging solution can displace the cations present in the zirconium phosphate and replace them with sodium ions. The solution leaving the multi-use module can contain the displaced cations, along with any sodium ions that have not been bound to the zirconium phosphate. After the process, the zirconium phosphate exists as a recharged zirconium phosphate 15, containing only sodium ions bound to the zirconium phosphate.

The recharging solution in the method from FIG. 2 can comprise any sodium salt that will not interfere with the dialysis system. Table 1 shows a partial listing of potential sodium salts and exemplary concentration ranges for each. Non-limiting examples of sodium salt solutions that can be used include sodium chloride, sodium acetate, sodium citrate, sodium sulfate, sodium carbonate, sodium nitrate, or sodium phosphate. A person skilled in the art will understand that other sodium solutions can also be used to recharge the zirconium phosphate. The sodium concentration in the sodium solution can be set at any concentration. Because the efficiency of the recharging process is dependent on the concentration of the sodium salt used, in any embodiment of the first, second and third aspects of the invention, the preferred concentration of the sodium salt will be at least 1 M, and can be more concentrated, including saturated solutions. In any embodiment of the first, second and third aspects of the invention, the concentration can be between any of 1.0 M to saturated, 0.5 M to 1.5 M, 1 M to 2.0 M, 1.8 M to 3.5 M, or 3.0 M to 5.0 M.

TABLE 1

| Salt | Concentration Range |
| --- | --- |
| Sodium chloride | 1.0M to Saturated |
| Sodium acetate | 1.0M to Saturated |
| Sodium citrate | 1.0M to Saturated |
| Sodium bicarbonate | 1.0M to saturated |
| Sodium phosphate | 1.0M to saturated |

The amount of the sodium salt solution used can vary based on the amount of zirconium phosphate being recharged. The more of the sodium salt solution used, the more cations that will be displaced by the sodium ions. In any embodiment of the first, second and third aspects of the invention, the sodium solution can be at least 1 mL per gram of zirconium phosphate being recharged. A person skilled in the art will understand that if a lower sodium concentration is being used, then more of the solution may be necessary. Less of the sodium solution can be used if not all of the other cations need to be removed from the zirconium phosphate. In any embodiment of the first, second and third aspects of the invention, the volume of the sodium salt solution used can be between any of 0.5 mL per gram of zirconium phosphate to 30.0 mL per gram of zirconium phosphate, 1.0 mL per gram of zirconium phosphate to 9.0 mL per gram of zirconium phosphate, 3.0 mL per gram of zirconium phosphate to 15 mL per gram of zirconium phosphate, and 15.5 mL per gram of zirconium phosphate to 25 mL. The volume necessary for recharging the zirconium phosphate can depend on the concentration of the sodium salt solution and all other variables used during the recharging process that can affect the efficiency of the method as described herein. Because in any embodiment of the first, second and third aspects of the invention the recharging solution can be recirculated through the zirconium phosphate, the total volume of recharging solution necessary may be less than the ranges listed above. For example, if 1 mL of recharging solution per gram of zirconium phosphate is necessary, 0.5 mL of recharging solution per gram of zirconium phosphate can be used if the recharging solution is recirculated through the zirconium phosphate twice. In any embodiment of the first, second and third aspects of the invention, the methods and systems of the invention can reserve an ending portion of a recharging solution to recharge another zirconium phosphate cartridge. For example, if 10-liters of recharge solution are required to recharge a cartridge, the first 5-liters can effectively recharge 90% of the zirconium phosphate and the second 5-liters may recharge the remaining 10%. Therefore, the second 5-liters will contain a lower concentration of calcium, magnesium, potassium and ammonium. The second 5-liters can then be used to effectively recharge another zirconium phosphate cartridge. This will minimize the total volume of water required and the mass of salt needed in the recharge solution.

In any embodiment of the first, second and third aspects of the invention, the zirconium phosphate cartridge can be designed with extra zirconium phosphate capacity. By designing extra zirconium phosphate capacity into the cartridge, less of the recharging solution would be necessary. In any embodiment of the first, second and third aspects of the invention, extra zirconium phosphate capacity can be built into the zirconium phosphate cartridge so that only 50% or less of the recharge solution otherwise necessary for recharging is needed in terms of water, salt and time, to meet the functional requirements for a recharged zirconium phosphate cartridge.

The flow rate of the salt solution can be varied according to the needs of the recharging process. A slower flow rate through the zirconium phosphate can result in a more efficient recharging process, requiring less of the salt solution. A slower flow rate can also result in a longer time period to complete the recharging process. A person skilled in the art will understand that the flow rate can be adjusted based on the needs to conserve recharging solution and the time available. In any embodiment of the first, second and third aspects of the invention, the flow rate can be between 0.01 and 9.0 ml/min per gram of zirconium phosphate. In any embodiment of the first, second and third aspects of the invention, the flow rate can be between any of 0.5 to 8.0 ml/min per gram of zirconium phosphate, 1.5 to 4.0 ml/min per gram of zirconium phosphate, 2.5 to 3.5 ml/min per gram of zirconium phosphate, 2.3 to 7.6 ml/min per gram of zirconium phosphate, 3.9 to 7.2 ml/min per gram of zirconium phosphate, 5.6 to 6.3 ml/min per gram of zirconium phosphate, 2.3 to 8.8 ml/min per gram of zirconium phosphate, or 3.0 to 7.0 ml/min per gram of zirconium phosphate.

The temperature of the solution being passed through the zirconium phosphate can also affect the efficiency of the recharging process. In some cases increasing the temperature reduces the volume of recharge solution required to recharge the zirconium phosphate. In any embodiment of the first, second and third aspects of the invention, the temperature of the salt solution can be maintained in any range between about 20° C. to about 105° C., with the top temperature possible depending on the boiling point of the particular solution. For example, the ranges include 25° C. to about 80° C., 35° C. to about 75° C., 40° C. to about 70° C., 50° C. to about 60° C., 25° C. to about 50° C., 50° C. to about 75° C., or 60° C. to about 105° C.

In any embodiment of the first, second and third aspects of the invention, the recharging solution can be added to the zirconium phosphate and halted. The flow of the recharging solution through the zirconium phosphate can be halted using any control system of valves and shunts, or similar means wherein the recharging solution is retained in the zirconium phosphate for a pre-set period of time, and then the flow of the recharging solution re-started. Halting the flow of the solution passed through the zirconium phosphate can be performed at least once. Halting the flow of the recharging solution while the recharging solution is in the zirconium phosphate and retaining the recharging solution in the zirconium phosphate can increase the efficiency of the process by allowing more time for cations in the recharging solution to exchange with the cations bound to the zirconium phosphate. Halting the flow of the recharging solution can, therefore allow for a reduced amount of the solution to be used. In any embodiment of the first, second and third aspects of the invention, once the flow is restarted the recharging solution can be held in the zirconium phosphate again. This process can be repeated at least one more time, and for any number of times during the recharging of the zirconium phosphate. In particular, a portion of the solution passed through the zirconium phosphate to recharge zirconium phosphate can be recirculated and passed through the zirconium phosphate at least one more time.

In any embodiment of the first, second and third aspects of the invention, the flow of the recharging solution through the zirconium phosphate can be in the opposite direction through the zirconium phosphate as the spent dialysate during dialysis. Passing the recharging solution through the zirconium phosphate in the opposite direction as the dialysate can improve the efficiency of the recharging process.

In any embodiment of the first, second and third aspects of the invention, the recharging solution used in step 14 of the method shown in FIG. 2 can be a mixture of a sodium salt and acid. The acid can be any acid capable of donating an $H^+$ ion to the zirconium phosphate. Non-limiting examples include hydrochloric acid, sulfuric acid, phosphoric acid, citric acid, acetic acid, lactic acid, and formic acid. Table 2 shows a partial list of possible acids that can be used in the recharging process and non-limiting exemplary concentration ranges for each. The sodium salt concentrations can be as shown in Table 1. A person skilled in the art will understand that other acids are possible to use in the recharging solution. Using both an acid and a sodium salt as the recharging solution allows for a recharged zirconium phosphate that has both hydrogen and sodium ions present. The ratio of hydrogen to sodium ions can depend on the relative amounts of sodium and hydrogen ions present in the recharging solution. The dependence on the ratio can provide for fine tuning of the final ratio of sodium to hydrogen ions contained in the zirconium phosphate by making adjustments to the relative amounts or concentrations of the acid and sodium salt used. In general, a person of ordinary skill in the art will understand that fine tuning can mean to vary one or more parameters of a method, determining if the results are closer or farther from the desired results, and repeating the process of varying parameters and determining the results until the desired results are achieved. The steps of fine tuning can be implemented by a specific computer and the steps, data, and processing algorithms stored on a non-transitory computer medium. In addition to efficiency, accuracy, speed, the fine tuning steps in conjunction with the present methods and systems provide significantly more cost savings in the use of zirconium phosphate in dialysis systems.

In any embodiment of the first, second and third aspects of the invention, the acid concentration can be between 1 and 5000 mM. In any embodiment of the first, second and third aspects of the invention, the acid concentration can be between any of 100 mM and 4500 mM, 15 mM to 500 mM, 100 mM to 2500 mM, 250 mM to 4000 mM, or 500 mM to 5000 mM. A person of ordinary skill will understand that the relative concentrations of sodium and hydrogen ions bound to the recharged zirconium phosphate can depend on the amount of acid or salt added to the recharging solution, and the strength of the acid. A higher concentration of acid used can result in more hydrogen ions bound to the recharged zirconium phosphate. With a lower acid concentration, the recharged zirconium phosphate can have less hydrogen ions.

In any embodiment of the first, second and third aspects of the invention, the ratio of sodium to hydrogen ions bound to the recharged zirconium phosphate can be customized for a particular patient, based on the patient's needs. The composition of sodium and hydrogen ions in the zirconium phosphate can influence the pH and the bicarbonate concentration leaving the sorbent cartridge and the amount of bicarbonate that may need to be added to the dialysate to achieve a desired bicarbonate concentration in the dialysate entering the dialyzer. This is because excess acid can react with the bicarbonate to form carbon dioxide. Knowing the patient's starting urea and bicarbonate blood levels allows the selection of a desired sodium and hydrogen composition in the zirconium phosphate that would achieve the appropriate dialysate bicarbonate composition required for the patient and minimize or eliminate the need for addition of bicarbonate into the dialysate.

TABLE 2

| Acid | Concentration Range |
| --- | --- |
| Hydrochloric Acid | 10 mM-5000 mM |
| Sulfuric Acid | 10 mM to 5000 mM |
| Phosphoric Acid | 10 mM to 5000 mM |
| Citric Acid | 10 mM to 5000 mM |
| Acetic Acid | 10 mM to 5000 mM |
| Lactic Acid | 10 mM to 5000 mM |
| Formic Acid | 10 mM to 5000 mM |

The recharging solution used in step 14 of FIG. 2 can be a mixture of sodium salt and a buffer solution. A buffer solution can comprise a mixture of a weak acid and the conjugate base of the weak acid. An equilibrium can exist in a buffer solution between the relative concentrations of the acid and base. Adding or removing acid to the buffer solution causes a shift in the equilibrium. For example, removing hydrogen ions from the buffer solution, such as by binding the hydrogen ions to zirconium phosphate, will result in a shift in the equilibrium away from the base and towards the acid. As such, the buffer solution resists changes in pH because changes in $H^+$ concentration are compensated for by the shift in the acid/base equilibrium. Adding a buffer solution instead of only adding acid allows a greater ability to control the hydrogen to sodium concentration in the recharged zirconium phosphate because the buffer provides greater control over the pH of the solution. Further, because the buffer resists changes in pH, the sodium salt/buffer solution can be reused for multiple zirconium phosphate recharges and still generates the same ratio of hydrogen to sodium ions in the recharged zirconium phosphate. Any buffer that can operate in the specific pH desired for the recharging process as explained herein can be used. Non-limiting examples include sodium acetate and acetic acid, sodium monobasic-phosphate and sodium dibasic-phosphate, and sodium citrate and citric acid. Table 3 shows non-limiting examples of buffer solutions that can be used for recharging, and exemplary concentrations of the acid and base. One skilled in the art will understand that the buffer selected will be based on the desired pH of the solution required, which in turn will depend on the desired ratio of hydrogen to sodium on the recharged zirconium phosphate. A lower pH will result in more hydrogen ions bound to the zirconium phosphate, while a higher pH will result in less hydrogen ions bound to the zirconium phosphate. In any embodiment of the first, second and third aspects of the invention, the acid concentration can be between any of 0.0 M to saturated, 0.0 M to 0.1 M, 0.05 M to 0.5 M, 0.3 M to 1.0 M, 0.8 M to 2.0 M, 1.5 M to 3.0 M, or 2.5 M to 5 M. In any embodiment of the first, second and third aspects of the invention, the base concentration can be between any of 0.0 M to saturated, 0.0 M to 0.5 M, 0.3 M to 1.0 M, 0.8 M to 2.0 M, 1.5 M to 3.0 M, or 2.5 M to 5 M. In any embodiment of the first, second and third aspects of the invention, the pH of the buffer solution can be between any of about 4 and about 8, about 4.5 and about 6, about 6 and about 7, or about 5.5 and about 7.5. Using a buffer solution as the recharging solution allows fine-tuning of the sodium to hydrogen ion ratio on the recharged zirconium phosphate by making changes in the pH and concentrations of the salt and buffer. In any embodiment of the first, second and third aspects of the invention, the recharging solution can be about 3200 mM NaCl, about 800 mM sodium acetate and about 80 mM acetic acid. This results in zirconium phosphate with a sodium/hydrogen ratio that results in an effluent pH around 7.0. In any embodiment of the first, second and third aspects of the invention, the recharging solution can be about 3340 mM NaCl, about 220 mM sodium citrate and about 60 mM citric acid resulting in a zirconium phosphate with a sodium/hydrogen ion ratio that results in an effluent pH around 6.5. In any embodiment of the first, second and third aspects of the invention, the additional sodium salt can be omitted and only the buffer solution including the sodium salt of the acid used.

TABLE 3

| Buffer Solution | Acid Concentration Range | Base Concentration Range |
| --- | --- | --- |
| Sodium acetate/acetic acid | 0 to saturated | 0 to saturated |
| Sodium citrate/citric acid | 0 to saturated | 0 to saturated |
| Sodium monobasic phosphate/ sodium dibasic phosphate | 0 to saturated | 0 to saturated |

In any embodiment of the first, second and third aspects of the invention, a secondary function of the recharging process can be to disinfect the zirconium phosphate module. Introduction of acids with elevated temperatures as described herein can disinfect the module. The solutions and elevated temperatures can kill most of the bacteria or viruses that may be present in the module, creating a module that is substantially free from bacteria and viruses until the module is reused in a subsequent dialysis session. Achieving sufficient disinfection requires certain combinations of pH, temperature and exposure time. A person of ordinary skill in the art will understand that the pH and temperature of the recharge solution, along with the exposure time of the zirconium phosphate to the recharge solution can be varied to achieve proper disinfection.

Figure 3:
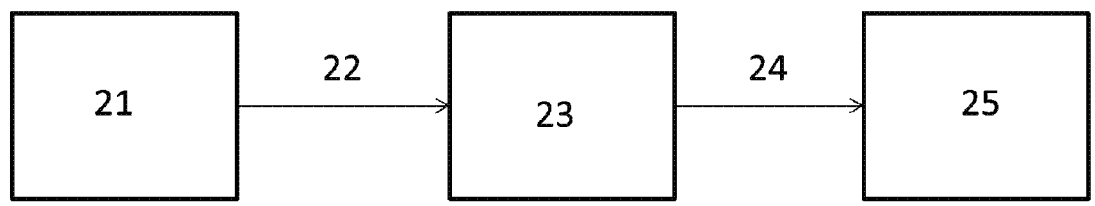
FIG. 3 shows a method of recharging zirconium phosphate by passing two different solutions through the zirconium phosphate.

Another method of the first, second and third aspects of the invention for recharging zirconium phosphate is shown in FIG. 3. The method begins with a used multi-use module containing zirconium phosphate that contains bound potassium, calcium, magnesium, and/or ammonium ions 21. In the first step of the recharging process 22 an acid solution can be passed through the multi-use module containing the zirconium phosphate. The acid can displace the cations present on the zirconium phosphate, replacing cations with hydrogen ions. The solution leaving the zirconium phosphate can contain the displaced cations, along with any remaining hydrogen ions that have not been bound to the zirconium phosphate. As above, the efficiency of the process will depend on the concentration of the acid solution used. In any embodiment of the first, second and third aspects of the invention, the concentration of the acid solution used in step 22 can be between any of 0.05 M to saturated, 0.05 M to 0.2 M, 0.1 M to 0.3 M, 0.2 M to 1 M, or 0.8 M to 5.0 M. However, a person skilled in the art will realize that the more concentrated the solution is, the more efficient the recharging process can be. After the first step of the recharging process, the zirconium phosphate can exist as zirconium phosphate, having only hydrogen ions bound 23.

In the second step 24 of the process shown in FIG. 3, a solution of sodium carbonate or combination of sodium hydroxide and sodium carbonate can be passed through the zirconium phosphate. The high sodium concentration in the solution can cause the displacement of any remaining cations other than hydrogen on the zirconium phosphate. The sodium solution can also displace some of the hydrogen ions bound to zirconium phosphate. The addition of sodium hydroxide to the sodium carbonate solution can improve the efficiency of the process of displacing hydrogen ions from the zirconium phosphate because the basic solution can drive the equilibrium in solution away from hydrogen ion formation, resulting in less hydrogen ions free to bind to the zirconium phosphate. The sodium solution leaving the zirconium phosphate can contain any remaining cations, hydrogen ions, and any unreacted sodium ions, resulting in a zirconium phosphate module having both sodium and hydrogen bound 25.

One skilled in the art will understand that the efficiency of the sodium displacement step in FIG. 3 can determine the final ratio of sodium to hydrogen ions on the zirconium phosphate. As such, the final ratio can be controlled using the flow rate of the sodium solution, the temperature of the sodium solution, the concentration of the sodium solution, or the amount of the sodium carbonate solution used. In any embodiment of the first, second and third aspects of the invention, the concentration of the sodium carbonate/sodium hydroxide solution can be between any of 0.05 M to saturated, 0.05 M to 0.2 M, 0.1 M to 0.3 M, 0.2 M to 1 M, or 0.8 M to 5.0 M, including saturated solutions. The ratio of sodium hydroxide/sodium carbonate used can vary between any of 0.0 and 1.0, 0.5 to 1.5, 1 to 2 or 1.5 to 3.

In any embodiment of the first, second and third aspects of the invention, the order of steps 22 and 24 can be reversed. That is, first a solution containing a sodium salt can be passed through the zirconium phosphate, exchanging the cations bound to the zirconium phosphate for sodium ions, so that the zirconium phosphate will have only sodium ions bound. Then, a solution of acid or buffer can be passed through the zirconium phosphate, displacing some of the sodium ions that were bound to the zirconium phosphate in the previous step with hydrogen ions, so that the zirconium phosphate has both hydrogen and sodium ions bound. One skilled in the art will understand that the final ratio of hydrogen to sodium ions bound to the zirconium phosphate will depend on the concentration or pH of the acid or buffer used. By first passing a sodium salt solution through the zirconium phosphate, and then passing an acid or buffer solution through the zirconium phosphate, the amount of acid or buffer necessary for recharging the zirconium phosphate is reduced. This can save costs if the buffer salts or acids are more expensive than the sodium salts used. Further, there would be a reduced risk of degradation of the zirconium phosphate due to exposure of high amounts of non-pH neutral solutions, potentially at elevated temperature during recharging.

Figure 4:
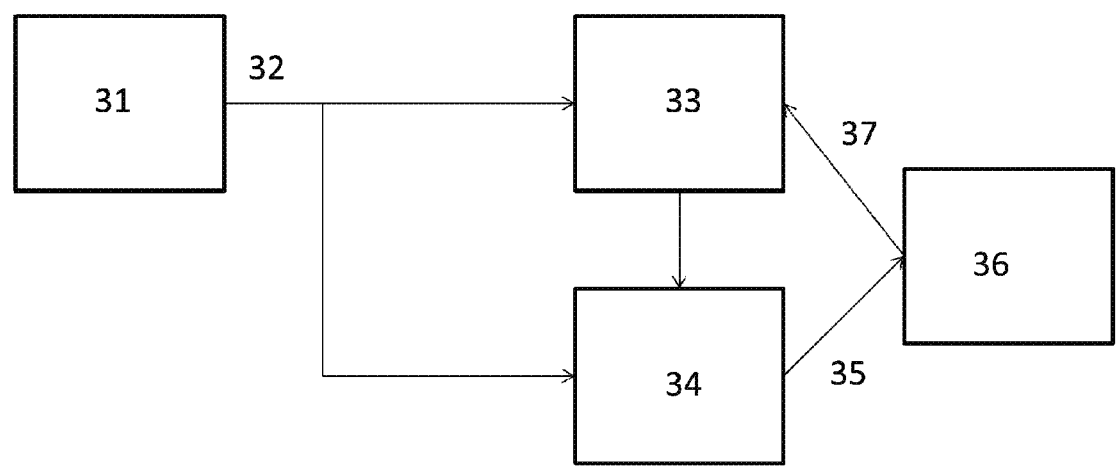
FIG. 4 shows a method of recharging zirconium phosphate by recirculating a solution through the zirconium phosphate.

FIG. 4 shows a recirculation method for recharging zirconium phosphate. The process can begin with a multi-use module containing zirconium phosphate 31, which before recharging may contain potassium, calcium, magnesium, ammonium, or other cations bound to the zirconium phosphate. A solution of sodium hydroxide and sodium bicarbonate can be passed through the zirconium phosphate in step 32. As with other embodiments of the first, second and third aspects of the invention, the high sodium concentration in the solution used in step 32 can cause displacement of the ammonium and other cations bound to the zirconium phosphate, replacing them with sodium ions. Because the sodium hydroxide/sodium bicarbonate solution is highly basic, the ammonium ions displaced can be converted into ammonia. The solution leaving the zirconium phosphate can therefore contain ammonia and any other cations that were bound to the zirconium phosphate as represented by 34. The zirconium phosphate in the module can contain bound sodium ions, with a reduced amount of bound ammonium, potassium, calcium and magnesium ions, as represented by block 33. The recharging solution recovered from the multi-use module can be recirculated as described herein. The recirculating fluid can be treated in step 35 by passing the fluid through a degassing module, which can remove dissolved or undissolved gases, such as ammonia, from the solution. After passing through the degassing module, the solution can be substantially free of ammonia, as represented by block 36. The solution can be passed back into the zirconium phosphate in step 37 to continue the recharging process. The fluid exiting the multi-use module after passing back through the zirconium phosphate in step 37 can contain additional ammonia removed from the zirconium phosphate. The resulting zirconium phosphate can contain less ammonia and other cations, and additional sodium ions. The process of steps 35 and 37 can be repeated until all of the ammonium ions have been removed from the zirconium phosphate.

The degassing module described in FIG. 4 can be any degassing mechanism known in the art. This includes, but is not limited to, membrane contactors, and spargers. The precise mechanism of degassing the solution is flexible.

In any embodiment of the first, second and third aspects of the invention, the degassing module may be located within the recharging apparatus, such as in the basin (not shown) of the recharging apparatus 5 show in FIG. 1. As described herein, the basin of the recharging apparatus 5 in FIG. 1 can contain a pump (not shown) for pumping fluid that exits through the bottom of the multi-use module 7 back to the fluid inlet 6 for reintroduction of the fluid into multi-use module 7. In any embodiment of the first, second and third aspects of the invention, a degasser as described herein can also be placed in the fluid flow loop between the basin of the recharging apparatus 5 and the fluid inlet 6 of FIG. 1.

In any embodiment of the first, second and third aspects of the invention, a membrane contactor can be used to degas the solution. A membrane contactor degasser is a degasser comprising a hydrophobic semi-permeable membrane. The hydrophobic semi-permeable membrane can be porous or non-porous. Water cannot pass through the semi-permeable membrane, but gases can pass through the semi-permeable membrane. The gasses, such as ammonia, dissolved in the solution contacting the membrane can diffuse through the membrane and out of the solution. In any embodiment of the first, second and third aspects of the invention, a vacuum may be applied to the degassing module to further drive the diffusion of gases through the membrane.

In any embodiment of the first, second and third aspects of the invention a sparger can be used to degas the recharging solution prior to reintroduction of the recharging solution into the zirconium phosphate. Sparging involves passing bubbles of an inert gas, such as nitrogen, argon or helium, through a solution. As the bubbles of the inert gas rise through the solution, dissolved gases, such as ammonia, can enter the bubbles by diffusion. The inert gas bubbles can exit the solution, bringing the ammonia and other dissolved gases out as well.

In any embodiment of the first, second and third aspects of the invention, restrictors can be used to degas the solution before reintroducing the solution back into the zirconium phosphate. A restrictor is a flow restriction through which the solution is passed. Passing the solution through a restrictor can result in a reduced pressure within the fluid after passing through the restrictor. Gases are less soluble in water at lower pressures. As such, by passing the recharging solution through a restrictor, gases dissolved in the recharging solution may come out of solution as gas bubbles. The gas bubbles can be removed through diffusion. In any embodiment of the first, second and third aspects of the invention, a vacuum pump may be used to further reduce the pressure of the solution and increase the efficiency of degassing.

In embodiments of the first, second and third aspects of the invention without a degasser, or where acidic or neutral recharging solutions are used, the ammonia can be removed from the solution by creating a salt with low solubility, such as ammonium vanadate in step 35 of FIG. 4. Vanadate ions can be added to the solution after passing through the zirconium phosphate, causing the ammonium ions to form ammonium vanadate and precipitate out of solution. This can then be filtered out of the solution, creating a solution substantially free of ammonia or ammonium ions.

When base is added to the sodium solution, the high pH can cause the formation of calcium carbonate and magnesium carbonate with the calcium and magnesium ions displaced from the zirconium phosphate. These carbonate salts can precipitate out of solution and be removed by filtration. Because the calcium and magnesium ions are removed, the recharging solution may be reused without re-introducing calcium and magnesium ions to the zirconium phosphate. Chelators, such as citrate, can also be used to selectively precipitate out calcium, magnesium or other divalent cations from solution, enabling the recharging solution to be reused. In any embodiment of the first, second and third aspects of the invention where the recharging solution is filtered and reused, the filter can be placed in any location in the recharging flow loop as described herein.

In any embodiment of the first, second and third aspects of the invention, a water-miscible organic solvent can be added to the recharging solution to remove salts and enable reuse of the recharging solution. Non-limiting examples of water miscible organic solvents can include methanol, ethanol, isopropanol, or acetone. Ammonium, calcium, and potassium salts have low solubility in solutions that include organic solvents. Sodium salts tend to have higher solubility in such solutions. As such, the particular solvent and the amount of that solvent added can be controlled to cause precipitation of ammonium, potassium and magnesium salts, but to retain the sodium in solution. Filtration of the solution to remove the non-sodium salts can result in a recharging solution containing only sodium. The organic solvent can then be removed by distillation or membrane distillation to return a water solution containing sodium ions that can be reused for recharging zirconium phosphate.

In any embodiment of the first, second and third aspects of the invention, a portion of the recharging solution can be retained and reused with or without treatment to remove non-sodium cations. The portion of the recharging solution used late in the recharging process will contain less of the non-sodium cations than the portion of the recharging solution used early in the recharging process because there are less cations on the zirconium phosphate to remove. For example, if 10 L of a recharging solution is used to recharge a given amount of zirconium phosphate, the last 5 L of the solution may be reusable. If the majority of the non-sodium cations are removed in the first 5 L of the recharging process, then the last 5 L of the recharging solution will only have a small amount of non-sodium cations present. This process can lower the overall solution requirements for recharging multiple batches of zirconium phosphate. One skilled in the art will understand that the portion of the recharging solution retained and reused can be greater or less than one half. In any embodiment of the first, second and third aspects of the invention, the portion of the recharging solution can be between any of 1-95%, 1-10%, 5-15%, 10-30%, 25-50%, 25-75%, 30-60%, 50-95%, or 75-95%.

The methods of recharging zirconium phosphate of the first, second and third aspects of the invention encompass recharging zirconium phosphate that has any combination of cations present at the beginning of the recharging process. For example, the same methods can be used to recharge zirconium phosphate that only has bound potassium ions, or any other cation, in order to obtain zirconium phosphate with sodium and hydrogen ions bound instead. In any embodiment of the first, second and third aspects of the invention, the methods disclosed can include treating the zirconium phosphate with a solution containing some cation, such as potassium, prior to recharging the zirconium phosphate with sodium and/or hydrogen ions. In any embodiment of the first, second and third aspects of the invention, the methods described herein can be used to change the sodium and hydrogen ratio present on the zirconium phosphate, even if the zirconium phosphate has only sodium and hydrogen ions bound at the start of the recharging process. For example, if the zirconium phosphate has a sodium/hydrogen ion ratio of 5:1, and the desired sodium/hydrogen ratio is 10:1, the processes described herein can be used to obtain zirconium phosphate with the desired 10:1 sodium to hydrogen ion ratio. One skilled in the art will understand that changing the ratio of sodium to hydrogen ions present in the zirconium phosphate would be considered to be "recharging" of the zirconium phosphate in order to place the zirconium phosphate in condition for use.

Figure 5:
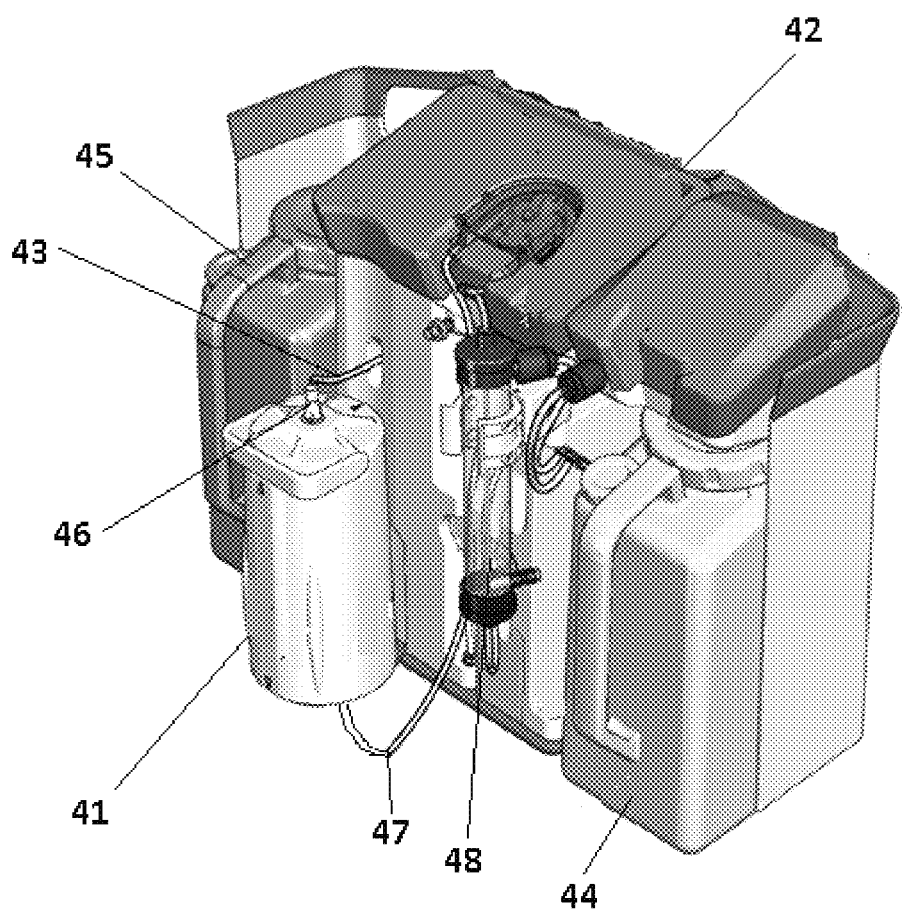
FIG. 5 shows a representative dialysis system that can use a rechargeable sorbent cartridge comprising zirconium phosphate.

One non-limiting embodiment of a sorbent dialysis system using a zirconium phosphate containing sorbent module is shown in FIG. 5. In use, an extracorporeal circuit (not shown) will flow blood from a patient to the dialyzer 48 and back to the patient. In the dialyzer 48, solutes in the blood can pass through a semi-permeable membrane (not shown) and enter dialysate that is passed through the dialyzer 48 in the opposite direction. Dialysate containing the toxins from the patient's blood is spent dialysate. In order to remove the toxins and other waste species present in the patient's blood from the spent dialysate so that the spent dialysate can be recirculated back to the dialyzer, the spent dialysate can be passed through sorbent cartridge 41. The sorbent cartridge 41 can comprise sorbent materials capable of removing specific toxins and waste species from the spent dialysate. Zirconium phosphate is a commonly used sorbent material. In any embodiment of the first, second and third aspects of the invention, the sorbent cartridge 41 can be split into two or more modules that are fluidly connected, such as a multi-use module and single use module as explained herein.

Urea present in the patient's blood can pass into the dialysate. Urease can be present in the sorbent cartridge to catalyze the breakdown of urea to ammonia and carbon dioxide. The ammonia is removed by the zirconium phosphate, where the ammonia present as ammonium ions binds to the zirconium phosphate, displacing hydrogen or sodium ions. The zirconium phosphate can also remove other cations from the spent dialysate, such as potassium, calcium or magnesium. The sorbent cartridges of the present invention can include other sorbent materials, including zirconium oxide, alumina, silica, activated carbon and ion-exchange resins.

After a dialysis session is finished, the zirconium phosphate in the sorbent cartridge 41 can contain ammonium, magnesium, calcium and potassium ions that need to be removed and replaced with hydrogen and/or sodium prior to the next dialysis session. The recharging process described herein can place the zirconium phosphate present in the sorbent cartridge 41 back into the proper condition for use.

During dialysis, the spent dialysate can enter the sorbent cartridge through an inlet connector (not shown), and exit through outlet connector 46. The inlet connector can be fluidly connected to the rest of the dialysis circuit by inlet line 47. The outlet connector can be fluidly connected to the rest of the dialysis circuit by outlet line 43. The dialysis circuit, including any infusate system, pumps or other apparatuses can be contained within dialysis cabinet 42. Water reservoir 45 can be used to provide clean water for priming and disinfection of the system, and to provide any necessary fluid for addition to the patient. Ultrafiltrate reservoir 44 can be used to hold fluid removed from the patient by ultrafiltration. Ultrafiltration is a process whereby fluid is removed from the dialysis circuit, causing additional fluid to move across the semi-permeable membrane of the dialyzer 48, and cause a net withdrawal of fluid from the patient's blood.

In any embodiment of the first, second and third aspects of the invention, the ultrafiltration reservoir 44 can be fluidly connected to the dialysis circuit at a point downstream of the sorbent cartridge 41. In such embodiments of the first, second and third aspects of the invention, the fluid removed by ultrafiltration can be free of any toxins or other solutes removed in the sorbent cartridge 41. Because the ultrafiltrate may not contain any cations other than sodium and hydrogen, such as potassium, magnesium, calcium or ammonium, if the ultrafiltrate is removed from the dialysate after passing through the sorbent cartridge the ultrafiltrate can be used as part of the recharging solution. If the ultrafiltration reservoir 44 is fluidly connected to the dialysis circuit at a point upstream of any infusate addition points, then the fluid removed by ultrafiltration can be free from any additional cations that are added to the dialysate by an infusate system, such as potassium, calcium or magnesium. Where the ultrafiltrate reservoir 44 is fluidly connected between the sorbent cartridge 41 and any infusate addition points, the fluid removed by ultrafiltration and added to the ultrafiltration reservoir 44 can contain only sodium and hydrogen ions that were displaced from the zirconium phosphate in the sorbent cartridge 41 and anions such as chloride and bicarbonate. The ultrafiltrate will be free from potassium, calcium, magnesium and ammonium. This ultrafiltrate fluid, collected during a dialysis session from fluid that has passed through the sorbent cartridge, in any embodiment of the first, second and third aspects of the invention, can be used as at least part of the recharging solution in recharging the zirconium phosphate. Even in embodiments of the first, second and third aspects of the invention where the ultrafiltrate reservoir 44 is fluidly connected at a point upstream of the sorbent cartridge, the ultrafiltrate can be used as a recharging solution. The solution will contain potassium, magnesium and calcium, but may contain these cations in concentrations low enough to still recharge the zirconium phosphate. Reuse of the ultrafiltrate as a recharging solution can reduce the overall water requirements for the sorbent dialysis system. In any embodiment of the first, second and third aspects of the invention, acid or additional sodium salts can be added to the ultrafiltrate to generate a recharging solution as explained herein. The amount of acid or sodium salts added to the ultrafiltrate to generate a recharging solution can depend on the desired ratio of sodium to hydrogen ions in the recharged zirconium phosphate, as explained herein.

In one example of the process for recharging zirconium phosphate, zirconium phosphate can be loaded with about 1 mEq of cations per gram of zirconium phosphate. The cations can be about 0.69 mEq ammonium per gram of zirconium phosphate, about 0.17 mEq potassium per gram of zirconium phosphate, about 0.10 mEq calcium per gram of zirconium phosphate and about 0.04 mEq magnesium per gram of zirconium phosphate. One skilled in the art will understand that the specific ratios of cations listed are for exemplary purposes and that any combination of cation is contemplated by the invention. The actual ratios of cations loaded on the zirconium phosphate can be varied and encompass any mEq of each of the cations, and can depend on the patient dialyzed.

A buffer solution can be passed through the zirconium phosphate. The volume of the buffer solution can be about 3 mL per gram of zirconium phosphate. The buffer solution can contain sodium chloride at a concentration of about 3340 mM, sodium citrate tribasic at a concentration of about 220 mM, and citric acid at a concentration of about 60 mM. The buffer solution can be passed through the zirconium phosphate at a rate of about 0.1 mL/min, and at a temperature of about 80° C. In any embodiment of the first, second and third aspects of the invention, the buffer solution can contain sodium chloride at a concentration range from about 2500 to 4000 mM, sodium citrate tribasic at a concentration range from about 100 to 350 mM, and citric acid at a concentration of about 10 to 100 mM. The buffer solution can be passed through the zirconium phosphate at a rate ranging from about 0.1 to 20 mL/min, and at a temperature range from about 50 to 98° C.

One of ordinary skill would understand all of the ranges as provided herein list a sufficient number of illustrative range species to support any range contained within the provided range. For example, a range of 0.1 to 20 mL/min support any of 0.6 to 19.9 mL/min, 0.1 to 0.2 mL/min, 18.8 to 18.9 mL/min, 9.9 to 10 mL/min, etc.

One, non-limiting example of the recharging process is described herein. Sodium zirconium hydrogen phosphate (Zirconium Phosphate), 20.9 grams, (MEL Chemicals, Manchester, England) was added to a 1 inch diameter jacketed column (Ace Glass, Vineland N.J.). Breakthrough solution was pumped through the column at approximately 10 ml per minute using a Masterflex peristaltic pump and silicone tubing. The breakthrough solution was pumped through the column, with constant concentrations of the following: 3 mM potassium chloride (Sigma-Aldrich, St. Louis Mo.), 1.5 mM calcium chloride dihydrate (Sigma-Aldrich, St. Louis Mo.), 0.5 mM magnesium chloride hexahydrate (Sigma-Aldrich, St. Louis Mo.), 20 mM ammonium chloride (Sigma-Aldrich, St. Louis Mo.), 105 mM sodium chloride (Sigma-Aldrich, St. Louis Mo.) and 25 mM sodium bicarbonate (Sigma-Aldrich, St. Louis Mo.). The pH of the solutions was brought to 7.4 using hydrochloric acid (Sigma-Aldrich, St. Louis Mo.).

The effluent from the column was passed through an in-line pH sensor (Mettler-Toledo, Billerica Mass.) and an in-line ammonium ion-selective electrode (Cole-Parmer, Vernon Hills Ill.). The in-line ammonium sensor was monitored until the effluent ammonium concentration reached approximately 6 mM, at which point the feed solution was reduced to a flow rate of zero and the zirconium phosphate column was ready to be recharged.

The zirconium phosphate column was recharged by passing a recharge solution of 3200 mM sodium chloride (Sigma-Aldrich, St. Louis Mo.), 800 mM sodium acetate (Sigma-Aldrich, St. Louis Mo.) and 80 mM of acetic acid (Sigma-Aldrich, St. Louis Mo.). The recharge solution was pumped through the column using a Masterflex peristaltic pump at a flow rate of 8 ml/min. The recharge solution was passed through the column in the opposite direction as the breakthrough solution. The recharge solution was pre-heated to 80° C. with a heat exchanger and the jacketed Ace column (Ace Glass, Vineland N.J.) was also heated to 80° C. with a recirculating water bath. 80-ml of recharge solution was passed through the column and the column was then rinsed with 10-ml of deionized water at 25° C.

Figure 6:
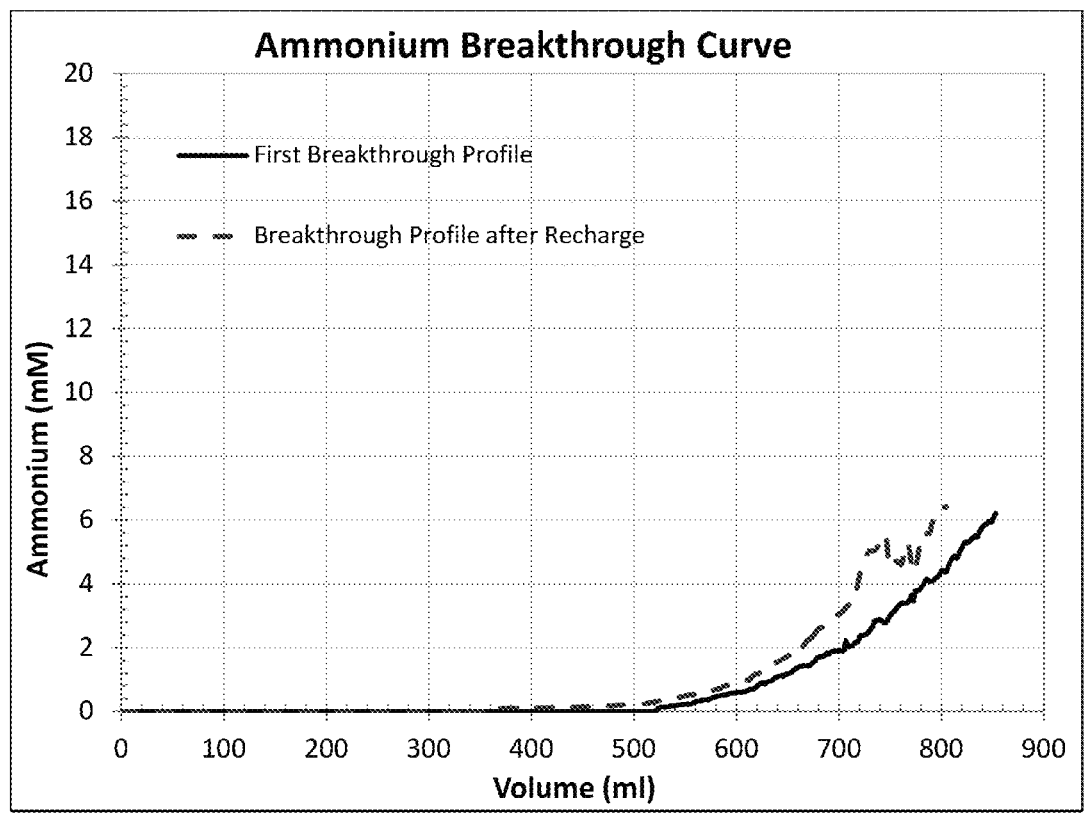
FIG. 6 shows a typical ammonium breakthrough profile before and after recharging of a zirconium phosphate module.
Figure 7:
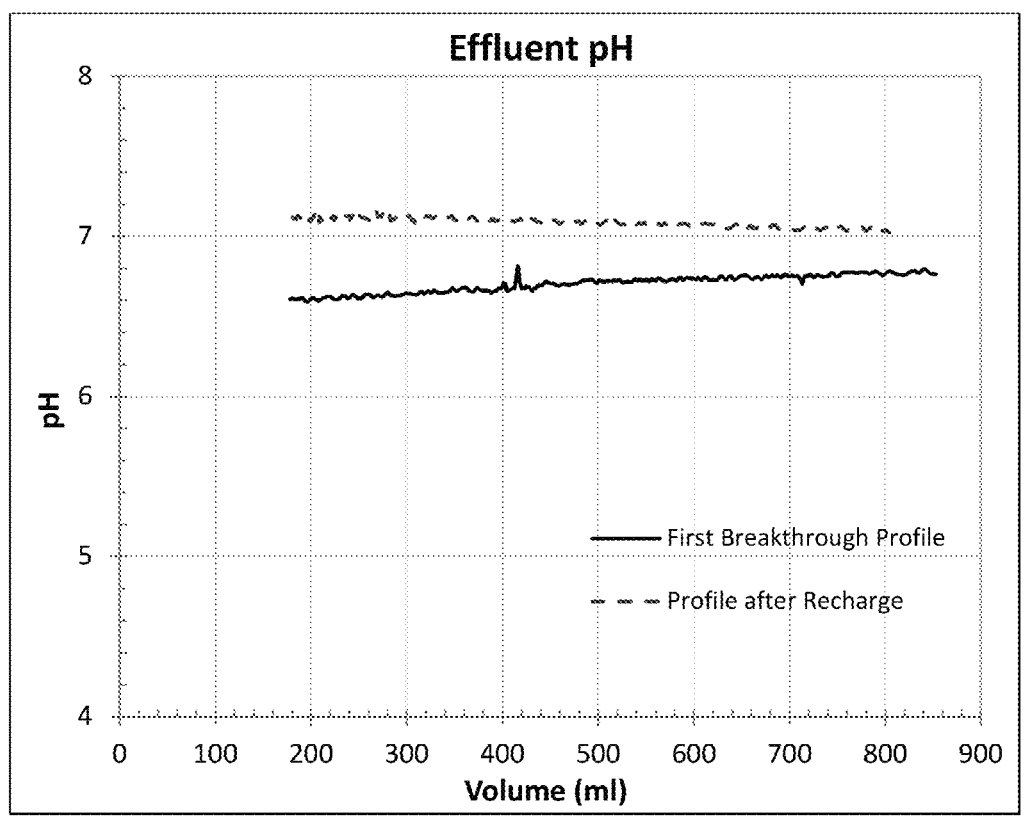
FIG. 7 shows a typical effluent pH profile before and after recharging of a zirconium phosphate module.

The recharged zirconium phosphate column was then tested with the breakthrough solution described above to determine the breakthrough ammonium profile and the effluent pH after recharging in comparison to the column performance before the recharging. FIG. 6 shows the ammonium breakthrough profile before (solid line) and after (dashed line) recharging the zirconium phosphate column. The profiles shown in FIG. 6 are similar, indicating that the ammonium capacity has returned to the zirconium phosphate. FIG. 7 shows the effluent pH profile before (solid line) and after (dashed line) recharging the zirconium phosphate column. The effluent pH after recharging is around 7, also showing that the ammonium capacity has returned to the zirconium phosphate.

Figure 8:
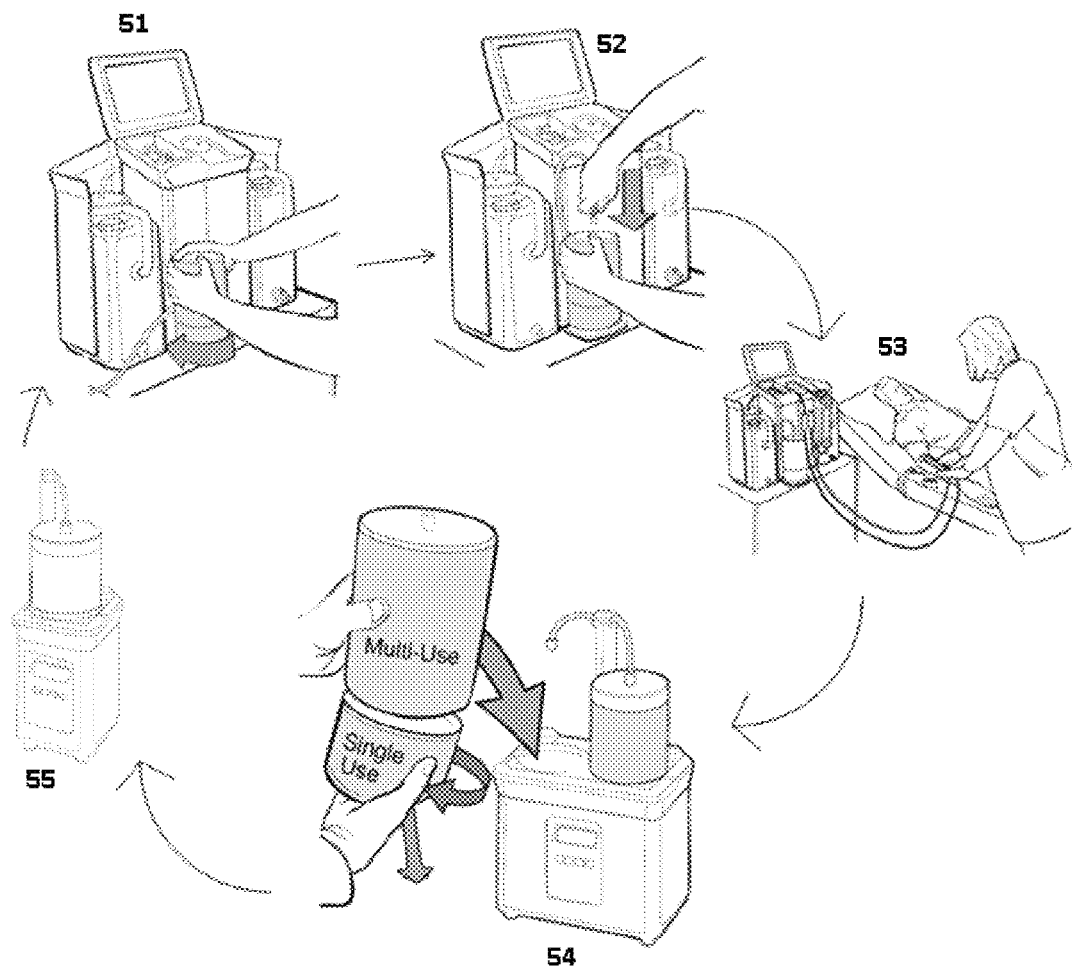
FIG. 8 is shows the steps of preparing a dialysis session, conducting dialysis, and recharging a module containing zirconium phosphate.

The direction of flow of the buffer through the zirconium phosphate can be in the opposite direction of flow that dialysate travelled through the zirconium phosphate during dialysis, as explained herein. One skilled in the art will understand that modifications to the concentrations of the components of the buffer solution, the amount of buffer solution, the temperature, and the flow rate, can be made and still be within the scope of the invention. A flow chart showing the steps for utilizing the method of the invention is shown in FIG. 8. In step 51, the multi-use module of a sorbent cartridge can be connected to the single use module of a sorbent cartridge to create a sorbent cartridge capable of being used in dialysis. In step 52 the user can ensure that the zirconium phosphate in the multi-use module has been recharged and that the single use module has not been previously used. In any embodiment of the first, second and third aspects of the invention, the recharging process can be tracked by the use of bar codes or RFID tags in order to keep track of whether the multi-use module has been recharged. After ensuring that both the single use and multi use modules are ready to be used, the sorbent cartridge can be connected to the dialysis system. In step 53, the patient can be connected to an extracorporeal circuit attached to the dialysis machine to circulate the patient's blood, and a dialysis session can be carried out and the patient treated. After dialysis, in step 54, the sorbent cartridge can be disconnected from the dialysis system. The multi-use module can be separated from the single use module in step 54 as explained herein. The single use module can be discarded, or sent to a recycling, replenishing or recharging facility. The multi-use module can be connected to a recharger and recharged in step 55. The multi-use module, after recharging, can be connected to a new single use module and reused starting again at step 51.

In any embodiment of the first, second and third aspects of the invention, the multi-use module, containing zirconium phosphate, can be stored for a period of time before reuse. In order maintain the zirconium phosphate with the correct ratio of hydrogen to sodium ions within the module, the multi-use module can be filled with a buffer solution for the storage. The buffer solution can be any of the solutions described above as used in the recharging process. In any embodiment of the first, second and third aspects of the invention, the buffer solution used during storage can have a pH of between about 6 and about 8.

The fluid connections connecting the multi-use module to the single use module can be any type of connections known in the art. The connections can be permanently placed on each of the modules, or can be separate components that can be attached to each of the modules for connection.

Figure 9A:
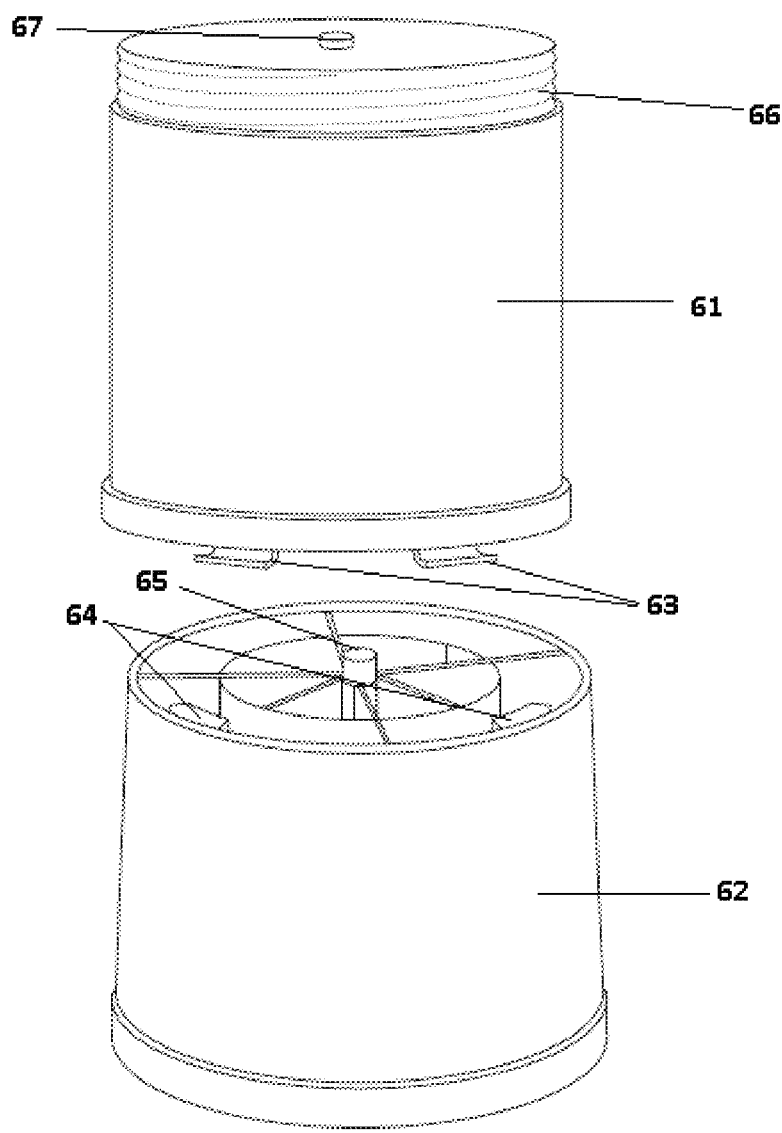
FIG. 9*a* shows a single use module and a multi-use module that can be connected.

In any embodiment of the first, second and third aspects of the invention, engagement members can be disposed on both the multi-use and single use modules, as shown in FIG. 9a. The engagement members can provide complementary joining or attachment of the single use modules into a particular configuration. The engagement members can allow for compartments to cooperatively engage. In any embodiment of the first, second and third aspects of the invention, these engagement members may be clasps, latches, or any known releasable fastening means. In general, the engagement members can interact to form a cooperative engagement and prevent inadvertent detachment of the multi use module from the single use module. For example, the multi-use module 61 can have engagement members 63 disposed around the bottom circumference of the module 61. The single use module 62 can have receiving grooves 64 for the engagement members 63. When the engagement members 63 from the multi use module 61 are inserted under the receiving grooves 64 on the single use module 62, the engagement members 63 can snap into place, locking the modules together. One skilled in the art will understand that the engagement members may be disposed on the top portion of the single use module, and the receiving grooves disposed on the bottom portion of the multi-use module. During use, fluid can enter through a fluid inlet (not shown) in the bottom of the single use module 62. After traveling through the single use module, the fluid can pass through fluid outlet 65 at the top of the single use module 62. When connected to the multi-use module 61, this fluid outlet 65 can fit into a fluid inlet (not shown) at the bottom of the multi-use module 61. After traveling through the multi-use module 61 fluid can exit through fluid outlet 67. The fluid outlet 67 can connect to the dialysis circuit as explained herein. Optional threaded portion 66 of the multi-use module 61 can be used to connect as a screw type connection to the dialysis circuit or recharger as explained herein.

Figure 9B:
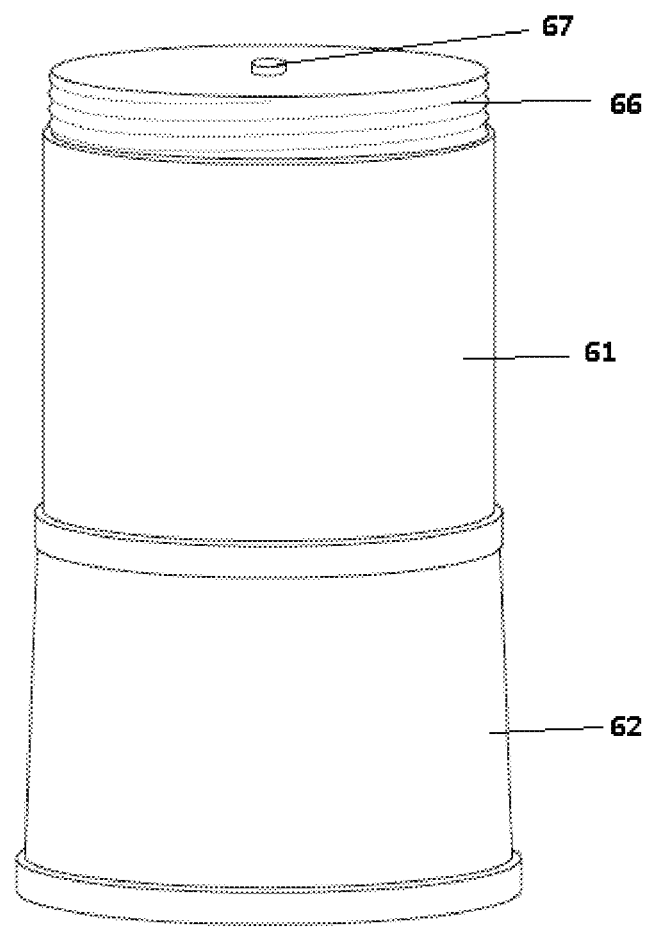
FIG. 9*b* shows a single use module and multi-use module connected together.

FIG. 9b shows the single use module 62 and multi-use module 61 when connected together. Fluid can travel through the single use module 62, and into the multi use module 61. Fluid can exit the combined modules through fluid outlet 67. In any embodiment of the first, second and third aspects of the invention, an o-ring or gasket can be disposed on the circumference of one or both of the modules to prevent leakage.

In any embodiment of the first, second and third aspects of the invention, the fluid connection between the single use module and the multi-use module can be a screw on variety. The single use module can have a threaded male portion of a screw connector disposed on the top of the module. The multi-use module can have a female receiving portion of a screw connector with internal threading disposed on the bottom of the module. In setting up the dialysis session, the user can place the single use module connector inside the multi-use module connector and twist the modules in opposite directions to secure the modules together. The interior of each portion of the screw type connection can be hollow, allowing fluid to flow from the single use module to the multi use module. One skilled in the art will understand that the male and female portions of the connector can be reversed, so that the male portion is on the multi-use module and the female portion is on the single use module.

In any embodiment of the first, second and third aspects of the invention, the screw connectors do not have to be hollow. Instead, grooves can be made on the exterior of the male portion of the screw connector. These grooves can be large enough to allow fluid to flow through the grooves and into the female receiving portion on the multi-use module. The grooves, once the modules are connected together, will be entirely inside the female portion, allowing fluid to flow between the modules without leakage.

In any embodiment of the first, second and third aspects of the invention, the connection between the single use module and the multi-use module can be a length of tubing. The tubing can attach to an attachment point at the outlet of the single use module, and to an attachment point at the inlet of the multi-use module. The tubing provides for a fluid pathway from the single use module to the multi-use module.

Alternatively, in any embodiment of the first, second and third aspects of the invention, the top of the single use module and the bottom of the multi-use module can both have a number of fluid channels or passageways built thereon. In any embodiment of the first, second and third aspects of the invention, these passageways can simply be holes drilled in the top or bottom surface of the respective modules. In any embodiment of the first, second and third aspects of the invention, the channels can extend into the interior of the respective modules. The outer portions of the single use and multi use modules can connect together in such a way as to prevent leakage of fluid passing between the modules. The modules can connect with screw type fittings or any other method known in the art. In any embodiment of the first, second and third aspects of the invention, gaskets or o-rings can be placed on the outer edges of the modules to ensure proper sealing when connected. In use, the fluid from the single use module can pass through the passages or channels in the top of the single use module, and then through the channels or passages in the multi-use module to enter the interior of the multi-use module.

Figure 10:
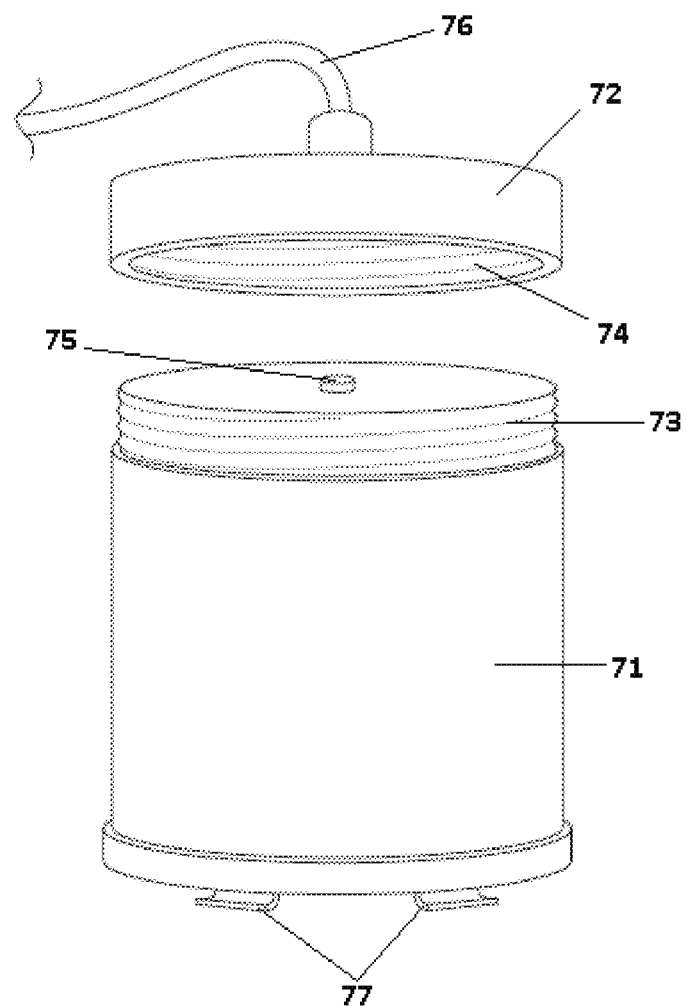
FIG. 10 shows a connection between a multi-use module and a recharger.

One embodiment of a connection for connection of a multi-use module to a recharger of the first, second and third aspects of the invention is shown in FIG. 10. Multi-use module 71 can have a threaded portion 73 at the top of the module 71. The recharger connector 72 can have a complimentary threaded portion 74 on the interior of the recharger connector 72. The recharger connector 72 can fit over the top of multi-use module 71 and when turned screw onto the multi-use module 71 to form the connection. During recharging, fluid can be passed through hose 76, and into the multi-use module 71 through inlet 75. Engagement members 77 can be used to facilitate connection to the basin of the recharger as explained herein. In any embodiment of the first, second and third aspects of the invention, the bottom portion of the multi-use module 71 can also have a threaded portion, and the module 71 can connect to the basin of the recharger in the same fashion as the top.

Figure 11:
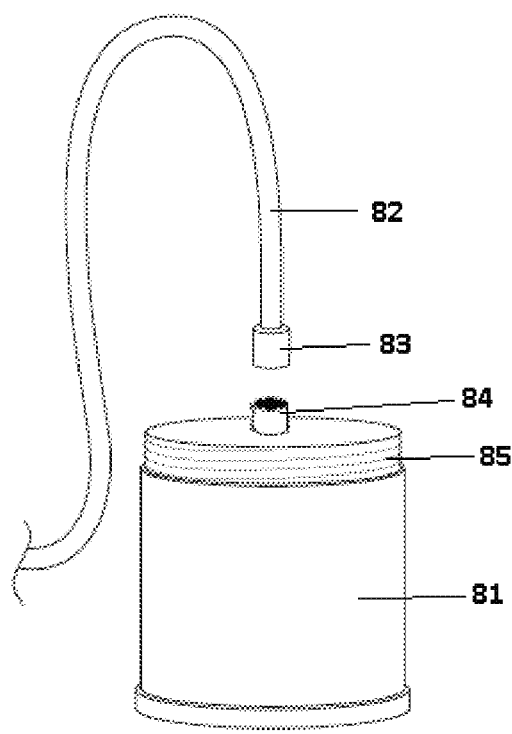
FIG. 11 shows a connection between a sorbent module and a dialysis system.

One embodiment of a connection between the module and the dialysis system of the first, second and third aspects of the invention is shown in FIG. 11. The sorbent module 81 can connect to a hose or tubing 82 through connector 83. The connector 83 can fit over fluid outlet 84 at the top of the sorbent module 81. Fluid from the sorbent module 81 can exit through the fluid outlet 84 and enter the tubing 82 through connector 83. In any embodiment of the first, second and third aspects of the invention, connector 83 can be a clamp, such that the connector 83 tightens around the fluid outlet 84 when turned. In any embodiment of the first, second and third aspects of the invention, the tubing 82 can be secured to the fluid outlet 82 with the use of external clamps, wires or other means. In any embodiment of the first, second and third aspects of the invention, fluid outlet 84 can have a threaded exterior, and connector 83 can have a complimentarily threaded interior, such that the fluid outlet 84 can be connected to connector 83 in a screw-type fashion. In any embodiment of the first, second and third aspects of the invention, the connection to the dialysis system can be similar to the connection to the recharger shown in FIG. 10, utilizing threaded portion 85 of the sorbent module 81.

In any embodiment of the first, second and third aspects of the invention, the connectors on the top and bottom of each of the modules can be separate from the modules themselves. That is, the connectors can attach to the modules and need not be formed integrally with the modules. The connectors can be fastened to the module in any fashion known in the art, such as with screws or bolts. The connectors can be removed and different connectors added as necessary, such as with connector 11 in FIG. 1. For example, the fluid connectors that connect the multi-use module to the single use module can be different from the fluid connector that connects the multi-use module to the recharging apparatus as explained herein. The user need only remove the connector from the multi-use module after a dialysis session and then replace the connector with the proper connector to connect to the recharging apparatus. One skilled in the art will understand that any type of fluid connection can be used without detracting from the scope of this invention. Any type of fluid connections described for connecting two modules, a module to the dialysis system, or a module to the recharging apparatus, can be used for any of the fluid connections of the invention.

One skilled in the art will understand that various combinations and/or modifications and variations can be made in the described systems and methods depending upon the specific needs for operation. Moreover features illustrated or described as being part of an aspect of the invention may be used in the aspect of the invention, either alone or in combination.

We claim:
1. A method, comprising the steps of:
    recharging zirconium phosphate in a reusable sorbent module by passing a solution of any one of an acid, a sodium salt, and combinations thereof, through the reusable sorbent module containing the zirconium phosphate.
2. The method of claim 1, wherein the solution contains a sodium salt; and wherein the sodium salt is selected from the group consisting of sodium chloride, sodium acetate, sodium phosphate, sodium sulfate, sodium carbonate, sodium nitrate, and sodium citrate; wherein the concentration of the sodium salt passed through the zirconium phosphate is between any of 0.05 M to saturated, 0.05 M to 1.5 M, 1 M to 2.0 M, 1.8 M to 3.5 M, and 3.0 M to 5.0 M; and wherein a volume of the solution passed through the zirconium phosphate is between any of 0.5 mL per gram of zirconium phosphate to 30 mL per gram of zirconium phosphate, 1.0 mL per gram of zirconium phosphate to 10 mL per gram of zirconium phosphate, 3.0 mL per gram of zirconium phosphate to 15 mL per gram of zirconium phosphate, and 0.5 mL per gram of zirconium phosphate to 20 mL per gram of zirconium phosphate.
3. The method of claim 1, further comprising:
    maintaining a temperature of the solution of any one of an acid, a sodium salt, and combinations thereof, at between about 20 ° C. and about 105 ° C.
4. The method of claim 1, wherein the flow rate of the solution passed through the zirconium phosphate is between any of 0.01 to 9.0 ml/min per gram of zirconium phosphate, 0.1 to 1 ml/min per gram of zirconium phosphate, 0.5 to 2.0 ml/min per gram of zirconium phosphate, 1.5 to 4.0 ml/min per gram of zirconium phosphate, and 3.0 to 7.0 ml/min per gram of zirconium phosphate.
5. The method of claim 4, further comprising:
    halting the flow of the solution passed through the zirconium phosphate at least once;
    retaining the solution in the zirconium phosphate for a pre-set period of time; and
    re-starting the flow of the solution passing through the zirconium phosphate after the pre-set period of time.
6. The method of claim 1, wherein the direction of flow of the solution through the zirconium phosphate is in an opposite direction of a flow of spent dialysate directed through the zirconium phosphate during a dialysis session.
7. The method of claim 1, wherein the solution comprises an acid, and wherein the acid is selected from the group consisting of sulfuric acid, phosphoric acid, citric acid, acetic acid, formic acid, lactic acid, and hydrochloric acid; and wherein the acid concentration is between any of 1 mM to 5000 mM, 15 mM to 500 mM, 100 mM to 2500 mM, 250mM to 4000 mM, and 500 mM to 5000 mM.
8. The method of claim 1, wherein the method comprises passing a solution of a sodium salt and passing a solution of an acid through the zirconium phosphate, and wherein the solution of a sodium salt is passed through the zirconium phosphate, prior to the solution of acid being passed through the zirconium phosphate.

9. The method of claim 1, wherein the solution comprises an acid; and further comprising:
passing a solution of sodium hydroxide and sodium carbonate through the zirconium phosphate after the step of passing the acid solution through the zirconium phosphate.

10. The method of claim 9, wherein the solution of acid has a concentration between any of 0.05 M to saturated, 0.05 M to 0.2 M, 0.1 M to 0.3 M, 0.2 M to 1 M, and 0.8 M to 5.0 M; the solution of sodium hydroxide and sodium carbonate has a concentration between any of 0.05 M to saturated, 0.05 M to 0.2 M, 0.1 M to 0.3 M, 0.2 M to 1 M, and 0.8 M to 5.0 M; and
wherein the ratio of sodium hydroxide to sodium carbonate is between any of 0 to 3, 0.5 to 1.5, 1 to 2 and 1.5 to 3.0.

11. The method of claim 1, further comprising: adding a water miscible organic solvent to the solution passed through the zirconium phosphate; wherein the water miscible organic solvent is selected from the group consisting of methanol, ethanol, isopropanol, and acetone; filtering the solution after passing through the zirconium phosphate; and reusing the solution.

12. The method of claim 1, wherein at least a portion of the solution passed through the zirconium phosphate comprises ultrafiltrate collected during a dialysis session, wherein the ultrafiltrate comprises fluid that has passed through a sorbent cartridge, and wherein the ultrafiltrate does not comprise contain potassium, magnesium, calcium or ammonium.

13. A method, comprising the steps of:
recharging zirconium phosphate in a reusable sorbent module by passing a buffer solution comprising an acid and a sodium salt of a conjugate base through the reusable sorbent module containing zirconium phosphate; wherein the buffer solution is selected from the group consisting of sodium acetate and acetic acid, sodium monobasic-phosphate and sodium dibasic-phosphate, and sodium citrate and citric acid.

14. The method of claim 13, wherein a ratio of the concentrations of the acid to the conjugate base is determined by a ratio of hydrogen to sodium ions desired on the zirconium phosphate after recharging; and wherein a pH of the buffer solution is between any of about 4 and about 8, about 4.5 and about 6, and about 6 and about 7, and about 5.5 and about 7.5.

15. The method of claim 13, further comprising the step of: adding sodium chloride to the buffer solution.

16. The method of claim 13, further comprising passing a solution of a sodium salt through the zirconium phosphate prior to the step of passing the buffer solution through the zirconium phosphate.

17. A method, comprising the steps of:
recharging zirconium phosphate in a reusable sorbent module by passing a solution of sodium hydroxide and sodium bicarbonate through the reusable sorbent module containing zirconium phosphate.

18. The method of claim 17, wherein a concentration of the solution of sodium hydroxide and sodium bicarbonate is between any of 0.05 M to saturated, 0.05M to 0.2 M, 0.1 M to 0.3 M, 0.2 M to 1 M, and 0.8 M to 5.0 M, and wherein a ratio of sodium hydroxide to sodium bicarbonate is between any of 0 to 3, 0 to 1, 0.5 to 1.5, 1 to 2, and 1.5 to 3.

19. The method of claim 17, wherein the solution of sodium hydroxide and sodium bicarbonate is recirculated, and further comprising degassing the solution of sodium hydroxide and sodium bicarbonate, filtering the solution of sodium hydroxide and sodium bicarbonate, or both.

20. The method of claim 17, wherein the zirconium phosphate is contained in a rechargeable sorbent cartridge module, wherein the rechargeable sorbent cartridge module is capable of being detachably connected to at least one other sorbent cartridge module such that the modules are in fluid communication when connected.

* * * * *